US006255347B1

(12) United States Patent
Xiaotao et al.

(10) Patent No.: US 6,255,347 B1
(45) Date of Patent: Jul. 3, 2001

(54) METHODS AND COMPOSITIONS COMPRISING R-IBUPROFEN

(75) Inventors: Qian Xiaotao; Stephen D. Hall, both of Indianapolis, IN (US)

(73) Assignee: Advanced Research and Technology Institute, Bloomington, IN (US)

( * ) Notice: Subject to any disclaimer, the term of this patent is extended or adjusted under 35 U.S.C. 154(b) by 0 days.

(21) Appl. No.: 08/879,870

(22) Filed: Jun. 20, 1997

Related U.S. Application Data

(60) Provisional application No. 60/020,248, filed on Jun. 21, 1996.

(51) Int. Cl.$^7$ .................................................. A61K 31/19
(52) U.S. Cl. ............................................................. 514/570
(58) Field of Search ............................................. 514/570

(56) References Cited

U.S. PATENT DOCUMENTS

| | | | |
|---|---|---|---|
| 3,228,831 | 1/1966 | Nicholson et al. | 167/53 |
| 3,385,886 | 5/1968 | Nicholson et al. | 260/515 |
| 4,851,444 | 7/1989 | Sunshine et al. | 514/570 |
| 5,087,454 | 2/1992 | Duerholz et al. | 424/464 |
| 5,621,140 | 4/1997 | Schloemer et al. | 562/401 |
| 5,631,296 | 5/1997 | Birrenbach et al. | 514/570 |
| 5,955,504 * | 9/1999 | Wechter et al. | 514/568 |

FOREIGN PATENT DOCUMENTS

| | | | |
|---|---|---|---|
| 0 085 544 | 8/1983 | (EP) . | |
| 0 675 103 | 10/1995 | (EP) . | |
| WO 88/02632 | 4/1988 | (WO) . | |
| WO 95/17154 | 6/1995 | (WO) . | |
| WO 96/28148 | 9/1996 | (WO) . | |
| WO 98/09603 | 3/1998 | (WO) . | |
| WO 98/20864 | 5/1998 | (WO) | A61K/31/00 |

OTHER PUBLICATIONS

Abramson, et al., "Non-steroidal anti-inflammatory drugs: effects on a GTP binding protein within the neutrophil plasma membrane," *Biochem. Pharmacol.*, 41(11):1567–1573, 1991.
Anderson, et al., "Exact cleavage site of Alzheimer amyloid precursor in neuronal PC–12 cells," *Neuroscience Letters*, 128:126–128, 1991.
Bautista, et al., "In vivo latex phagocytosis primes the Kupffer cells and hepatic neutrophils to generate superoxide anion," *J. Leukocyte Biol.*, 51:39–45, 1992.
Bomalaski, et al., "Aspirin inhibits phospholipase C," *Biochem. Bioph., Res. Comm.*, 139(1):115–121, Aug. 1986.
Boneberg, et al., "Inhibition of cyclooxygenase–1 and –2 by R(–)– and S(+)–ibuprofen," *J. Clin. Pharmacol.*, 36:16S–19S, 1996.
Breitner, et al., "Inverse association of anti–inflammatory treatments and Alzheimer's disease: Initial Results of a co–twin control study," *Neurology*, 44:227–232, Feb. 1994.

Breitner, et al., "Delayed onset of Alzheimer's Disease with nonsteroidal Anti–inflammatory and histermine Hs Blocking Drugs," *Neurobiology of Aging*, 16(4):523–530, 1995.
Broda and Koff0., "NSAIDs: A profile of Adverse Effects" Hanely and Belfus, Inc. Philadelphia, PA, 1992.
Buckley et al., "Ketorolac: A Review of its Pharmacodynamic and Pharmacokinetic Properties, and Therapeutic Potential," *Drugs*, 39(1): 86–109, 1990.
Caldwell et al., "The Metabolic Chiral Inversion and Dipositional Enantioselectivity of the 2–Arylpropionic Acids and Their Biological Consequences," *Biochem. Pharmacol.*, 37(1): 105–114, 1988.
Caporaso, et al., "Protein phosphorylation regulates secretion of Alzheimer β/A4 amyloid precursor protein," *Proc. Nation. Acad. Sci. USA*, 89:3055–3059, Apr. 1992.
Castagna et al., "Direct activation of calcium–activated, phospholipid–dependent protein kinase by tumor–promoting phorbol–esters," *J. Biol. Chem.*, 257(13):7847–7851, Jul. 1982.
Cole, et al., "Decreased level of protein kinase C in Alzheimer Brain," *Brain Res.*, 452:165–174, 1988.
Driedger and Blumberg, "The effect of phorbol diesters on chicken embryo fibroblasts," *Cancer Res.*, 37:3257–3265, Sep. 1977.
Esch, et al., "Cleavage of amyloid β peptide during constitutive processing of its precursor," *Science*, 248:1122–1224, Jun. 1990.
Evans et al., "The Relationship Between the pharmacokinetics of Ibuprofen Enantiomers and the Dose of Racemic Ibuprofen in Humans," *Biopharmaceutics & Drug Disposition*, 11:507–518, 1990.
Giovannucci, et al., "Aspirin and the risk of colorectal cancer in women," *N. Engl. J. Med.*, 333(10):609–614, Sep. 1995.
Goldegraber, et al., "Characterization and chromosomal localization of a cDNA encoding brain amyloid of Alzheimer's Disease," *Science*, 235:877–880, Feb. 1987.
Hall et al., "Bioavailability of R and S Ibuprofen (I) in Humans," *Clin. Pharmacol. Ther.*, 51(2):130, Feb. 1992.
Hall et al., "Lack of Presystemic Inversion (R)– to (S)–Ibuprofen in Humans," *Clin. Pharmacol. and Therap.*, 53(4):393–400, Apr. 1993.
Heath et al., "Nonsteroidal Antiinflammatory Drugs and Human Cancer," *Cancer*, 74(10):2885–2888, Nov. 1994.

(List continued on next page.)

*Primary Examiner*—Jerome D. Goldberg
(74) *Attorney, Agent, or Firm*—Fulbright & Jaworski

(57) ABSTRACT

The present invention relates generally to the fields of chemotherapeutic treatments. More particularly, it concerns the use of ibuprofen, a non-steroid anti-inflammatory drug, in the treatments of disease. More particularly, it has been discovered that the R-enantiomer of ibuprofen, previously thought to be inactive, may be used as an antineoplastic agent and also in the prophylactic and therapeutic treatment of Alzheimer's and Alzheimer's related diseases.

8 Claims, 8 Drawing Sheets

OTHER PUBLICATIONS

Hixson, et al., "Antiproliferative effect of nonsteroidal anti-inflammatory drugs against human colon cancer cells," *Cancer Epidem. Biomar.& Prevent.*, 3:433–438, Jul./Aug. 1994.

International Search Report dated Dec. 11, 1997 (INDY:009P).

Jabert and Castonguay, "Effects of NSAIDs on NNK-induced pulmonary and gastric tumorigenesis in A/J mice," *Cancer Lett.*, 66:21–28, 1992.

Jamali, "Pharmacokinetics of Enantiomers of Chiral Non–Steroidal Anti–inflammatory Drugs," *European Journal of Drug Metabolism and Pharmacokinetics*, 13(1):1–9, 1988.

Jeffery et al., "The Site of Inversion of R(-)–Ibuprofen: Studies Using Rat In Situ Isolated Perfused Intestine/Liver Preparations," *J. Pharm. Pharmacol.*, 43:715–720, 1991.

Knights and Drew, "The Effects of Ibuprofen Enantiomers on Hepatocyte Intermediary Metabolism and Mitochomdrial Respiration," *Biochremical Pharmacology*, 44(7):1291–1296, 1992.

Kopp and Ghosh, "Inhibition of NF–κB by sodium salicylate and aspirin," *Science* 265:956–959, Aug. 1994.

Laine, "Nonsteroidal anti–inflammatory drug gastropathy," *Gastrointestinal Endoscopy Clinics of North America*, 6(3):489–504, Jul. 1996.

Lamph, et al., "Induction of proto–oncogene JUN/AP–1 by serum and TPA," *Nature*, 334:629–631, Aug. 1988.

Lang et al., "New Antiinflammatory Compounds that Inhibit Tumor Necrosis Factor Production: Probable Interaction with Protein Kinase C Activiation[1]," *The Journal of Pharmacology and Experimental Therapeutics*, 275(1):171–176, 1995.

Langman, et. al., "Risks of bleeding peptic ulcer associated with individual non–steroidal anti–inflammatory drugs," *Lancet*, 343:1075–1078, 1994.

Love, et al., "Levels of ornithine decarboxylase activity in patients with colon cancer, a family history of nonpolyposis hereditary colorectal cancer, and adenomas," *Cancer Epidem. Biomar.& Prevent.*, 1:195–198, Mar./Apr. 1992.

Marnett, "Aspirin and the potential role of prostaglandins in colon cancer," *Cancer Res.*, 52:5575–5589, Oct. 1992.

Mashiah, et al., "Protein kinase C alteration is an early biochemical marker in Alzheimer's Disease," *J. of Neurosci.*, 11(9):2759–2767, Sep. 1991.

Masters, et al., "Amyloid plague care protein in Alzheimer's disease and Downs Syndrome," *Proc. Natl. Acad. Sci. USA*, 82:4245–4249, Jun. 1985.

Matsushima, et al., "$Ca^{2+}$–Dependent and $Ca^{2+}$–independent protein kinase C changes in the brains of patients with Alzheimer's Disease," *J. of Neurochem.*, 67(1):317–323, 1996.

Menzel–Soglowek, "Metabolic Chiral Inversion of 2–Arylpropionates in Different Tumor Cell Lines," *Agents Actions*, 44:23–29, 1993.

Metha, et al., "Influence of thiols and inhibitors of prostaglandin biosynthesis on the carcinogen–induced development of mammary lesions in vitro," *Anticancer Res.*, 11:587–591, 1991.

Neidel, et al., "Phorbol ester receptor copurifies with protein kinase C," Proc. *Natl. Acad. Sci. USA*, 80:36–40, Jan. 1983.

Patterson, et al., "Activated neutrophils alter contractile properties of the pulmonary artery," *Am. J. Resp. Cell Mol. Biol.*, 6:260–269, 1992.

Price, et al., "Amyloidosis in aging and Alzheimer's disease," *Am. J. Pathol.*, 141(4):767–772, Oct. 1992.

Reddy, et al., "Inhibition of colon carcinogenisis by prostaglandin synthesis inhibitors and related compounds," *Carcinogenesis*, 13(6):1019–1023, 1992.

Rich, et al., "Nonsteroidal anti–inflammatory drugs in Alzheimer's Disease," *Neurology*, 45:51–54, 1995.

Robakis, et al., "Molecular cloning and characterization of a cDNA encoding the cerebrovascular and the neuritic plaque amyloid peptides," *Proc Natl. Acad Sci. USA*, 84:4190–4194, Jun. 1987.

Rogers, et al., "Clinical trial of indomethacin in Alzheimer's Disease," *Neurology*, 43:1609–1611, Aug. 1993.

Rudy et al., "Variability in the disposition of ibuprofen enantiomers in osteoarthritis patients," *Ther. Drug. Monit.*, 14(6):464–470, 1992.

Schoen and Vender, "Mechanisms of nonsteroidal anti–inflammatory drug induced gastric damage," *Am. J. Med.*, 86:449–458, Apr. 1989.

Shimohama, et al., "Assessment of protein kinase C isozymes by two–site enzyme immunoassay in human brains and changes in Alzheimer's Disease," *Neurology*, 43:1407–1413, Jul. 1993.

Sisodia, et al., "Evidence that β–amyloid protein in Alzheimer's Disease not derived by normal processing," *Science*, 248:492–495, Apr. 1990.

Slack, et al., "Regulation of Amyloid precursor protein release by protein kinase C in Swiss 3T3 fibroblasts," *Annals New York Academy of Sci.*, 695:128–131, 1993.

Stewart et al., "Risk of Alzheimer's Disease and Duration of NSAID Use," *Neurology*, 48:626–632, Mar. 1997.

Tanzi, et al., "Protease inhibitor domain encoded by an amyloid protein precursor mRNA associated with Alzheimer's Disease," *Nature*, 331:528–30, Feb. 1988.

Turner and Berkel, "Nonsteroidal anti–inflammaory drugs for the prevention of colon cancer," *Can. Med. Assoc. J.*, 149(5):595–602, 1993.

Vesela, et al., "Lack of inhibition of ornithine decarboxylase activity by ibuprofen," *Pharmacol. Res.*, 25(4):347–352, 1992.

Villanueva, et al., "Equipotent inhibition by R(-)–, S(+)– and racemic ibuprofen of human polymorphonuclear cell function in vitro," *Br. J. Clin. Pharmacol.*, 35:235–242, 1993.

Wechter, "Drug Chirality: On the Mechanism of R–Aryl Propionic Acid Class NSAIDs Epimerization in Humans and the Clinical Implications for the Use of Racemates," *J. Clin. Pharmacol.*, 34:1036–1042, 1994.

Xiaotao and Hall, "Enantioselective inhibition of neoplastic transformation in NIH 3T3 cells by ibuprofen," *FASEB J.*, 11(3):A303, Feb. 1997.

Xiaotao, et al., "Incorporation of R– and S–ibuprofen in to hybrid diacylglycerols and stimulation of protein kinase C in vivo," Abstract, *ISSX Proceedings*, 10:184, 1996.

* cited by examiner

*of post 7 days dose*

*of post 1st dose*

METHODS AND COMPOSITIONS COMPRISING R-IBUPROFEN

The present application claims the priority of co-pending U.S. Provisional Patent Application Ser. No. 60/020,248, filed Jun. 21, 1996. The entire text of the above-referenced disclosure is specifically incorporated by reference herein without disclaimer.

The government owns rights in the present invention pursuant to grant number RO1 DK37994 from the National Institutes of Health.

BACKGROUND OF THE INVENTION

1. Field of the Invention

The present invention relates generally to the fields of chemotherapeutic treatments. More particularly, it concerns the use of ibuprofen, a non-steroid anti-inflammatory drug, in the treatments of malignancies such as cancer. In other embodiments, the present invention relates to the therapeutic uses of ibuprofen in the treatments of Alzheimer's and Alzheimer's-related diseases.

2. Description of Related Art

Neoplastic diseases are conditions in which the abnormal proliferation of cells results in a cancerous mass of cells. These cancers are responsible for hundreds of thousands of deaths in the U.S. alone each year. Unfortunately, neoplasia possess a wide variety of abnormalities in structure and function that render them difficult to attack. Thus, new and effective treatments of neoplastic diseases are valuable for the prevention and/or cure of cancer.

Alzheimer's Disease is a complex pathology that affects 5 to 11% of the population over 65 years, and as much as 47% of the population over the age of 85 in developed countries. The health care cost per patient for this disease are staggering, given the severe physical and mental debilitation of the patients. If preventive measures are not found, the numbers can be expected to increase dramatically as the aging population increases (Flier and Underhill, 1991), further escalating costs.

A class of compounds with a potential therapeutic value in both of the aforementioned afflictions is non-steroidal anti-inflammatory drugs (NSAID). NSAIDs are commonly used as anti-inflammatory agents and as analgesics. Physiologically, these compounds are known to inhibit the biosynthesis of prostaglandins by inhibition of the cyclooxygenase enzyme (Buckley et al., 1990).

Ibuprofen is an NSAID that acts by inhibiting cyclooxygenase and omithine decarboxylase activities. However, it appears that this effect also is associated with a number of undesirable effects, including toxicity, because the inhibition of prostaglandin synthesis leads to gastrointestinal distress, possible renal and hepatic toxicities, and other malfunctions including thrombocytopenia and leukopenia (leading to subsequent agranulocytosis). Agranulocytosis is a life threatening condition that develops rapidly and is difficult to detect, and has been described for several NSAIDs including indomethacin, ketoprofen and ibuprofen. Thus, NSAIDs are contraindicated in patients whose immune systems are compromised by HIV infection, chemotherapy, ionizing irradiation, corticosteroids, immunosuppressives and the like and also in conditions such as emphysema, bronchiectasis, diabetes mellitus, leukemia and the like (Broda et al., 1992).

Ibuprofen, like many other NSAIDs, exhibits molecular chirality, and thus can be found in R- and S-enantiomeric forms. Such compounds typically are produced in enantiomeric mixtures which subsequently can be separated into the individual enantiomers (Yamaguchi et al., 1987). It is generally alleged that the S-enantiomer has the higher prostaglandin synthesis activity of the two enantiomers (Yamaguchi et al., 1987). Indeed Caldwell et al. (1988) have suggested that the R-isomer functions, at best, as prodrugs for the therapeutically active S-forms when the racemic drug is administered. Further, Caldwell et al. suggest that at worst the R-enantiomers of NSAIDs are undesirable impurities in an active drug causing difficulties due to non-stereoselective toxicity.

NSAIDs previously have been shown to be therapeutically effective against a variety of cancers (Heath et al., 1994). However, the toxicity and side effects of S-enantiomers, as described above, make NSAIDs unfavorable for use in human treatment. Indeed, many NSAIDs have been removed from common usage even as analgesics. It would be a fruitful endeavor to identify formulations of NSAIDs for use as treatments of cancers and other diseases, but without the aforementioned disadvantages of the S-enantiomeric compositions.

SUMMARY OF THE INVENTION

The present invention is directed to the provision of novel compositions and uses of ibuprofen. In particular, it has been discovered that the R-enantiomer of ibuprofen, previously thought to be inactive, may be used as a prophylactic and therapeutic agent in the treatment of diseases such as cancers, Alzheimer's and Alzheimer's related diseases."

Thus, in one embodiment, there is provided a method of inhibiting neoplastic transformation of a cell, comprising contacting the cell with an amount of an R-ibuprofen composition effective to inhibit neoplastic transformation of the cell. In particular embodiments, the tumor cell may be selected from the group consisting of cecum, colon, rectum, jejunum, duodenum, esophagus, stomach, pancreas, liver, bile duct, gall bladder, prostate gland, breast, kidney, pituitary gland, adrenal gland, thyroid gland, ovary, testicle, lung, brain, bone, blood and bone marrow cell.

In certain other embodiments, the cell further is exposed to a chemo- or radiotherapy. It is envisioned that the R-ibuprofen composition may be dispersed in a pharmaceutically acceptable excipient. In particular aspects, it is envisioned that the R-ibuprofen pharmaceutical composition is administered orally. An "R-ibuprofen composition" as used herein is a composition comprising enantiomerically enriched R-ibuprofen, R-ibuprofen substantially free from S-ibuprofen, or a substantially pure R-ibuprofen isomer.

In other embodiments, the cell is located within an animal. In preferred embodiments, the animal is a human subject. In particular embodiments, the animal has colorectal cancer. In yet other embodiments, the animal has an adenoma-based cancer. In preferred embodiments, the cancer may be cecum, colon, rectum, jejunum, duodenum, esophagus, stomach, pancreas, liver, bile duct, gall bladder, prostate gland, breast, kidney, pituitary gland, adrenal gland, thyroid gland, ovary, testicle, lung, brain, bone, blood or bone marrow cell cancer.

In other aspects of the present invention, there is provided a method of preventing cancer growth, comprising administering to an animal at risk for, or having cancer, an amount of an R-ibuprofen pharmaceutical composition effective to inhibit cancer growth in the animal. In particular aspects, the R-ibuprofen composition is for use in the preparation of a prophylactic formulation for administration to a patient at risk for developing cancer. In other embodiments the R-ibuprofen composition may be used for the preparation of a medicament for treating cancer. The R-ibuprofen may have a reduced toxicity and gastropathy as compared with a racemic mixture of R- and S-ibuprofen, or an enantiomerically pure S-ibuprofen composition.

The present invention further contemplates a method of treating cancer comprising administering to an animal with cancer a therapeutically effective amount of an R-ibuprofen pharmaceutical composition. In particular aspects, the method further comprises administering to the animal a therapeutically effective amount of at least a first selected anti-cancer agent In certain preferred embodiments, the anti-cancer agent is taxol, tamoxifen, cyclophosphamide, doxorubicin, 5-fluorouracil, tretinoin, all-trans retinoic acid, methotrexate, 5-azacytidine, daunarubicin, vinblastine, vincristine, ifosfamide, carboplatin, cisplatin, semustine, adriamycin, finasteride, raloxifene, melphalan, buthionine, cyclopentylcytosine, tiazofurin, cytarabine, carmustine, aspirin, flurbiprofen, piroxicam, sulindac, paclitaxel, glycerrhetinic acid, lonidamine, mitoguazone, homoharringtonine, topotecan, edatrexate or aminocampothecin.

Also provided by the present invention, is a composition comprising a combined effective amount of R-ibuprofen and a chemotherapeutic agent. The composition may be dispersed in a pharmaceutically acceptable excipient.

Another aspect of the invention provides a kit comprising, in suitable container means, R-ibuprofen and a chemotherapeutic agent.

In yet a further aspect, the present invention provides a method of inhibiting the production of amyloid β-protein in a cell, comprising contacting the cell with an amount of an R-ibuprofen composition effective to inhibit amyloid β-protein production in the cell. In particular aspects, the cell is a central nervous system cell.

In an alternative embodiment, the present invention describes a method of promoting the secretion of amyloid precursor protein from a cell, comprising contacting the cell with an amount of an R-ibuprofen composition effective to increase amyloid precursor protein secretion from the cell.

In a further aspect, the present invention contemplates a method of preventing or slowing the onset of Alzheimer's disease, comprising administering to an animal at risk for or having Alzheimer's disease an amount of an R-ibuprofen pharmaceutical composition effective to inhibit Alzheimer's disease in the animal. The composition may comprise an enantiomerically enriched R-ibuprofen for use in the preparation of a prophylactic formulation for administration to a patient at risk of developing Alzheimer's disease. In an alternative embodiments, the composition may be used in the preparation of a medicament for treating Alzheimer's disease. In other aspects, the present invention provides for the use of a composition comprising enantiomerically enriched R-ibuprofen in the preparation of a formulation or medicament for administration to a patient at risk of developing or having Alzheimer's disease.

In yet a further aspect, the present invention provides a method of treating Alzheimer's disease, comprising administering to an animal with Alzheimer's disease a therapeutically effective amount of a pharmaceutical composition comprising R-ibuprofen. In certain aspects, the method further comprises administering to the animal an anti-Alzheimer's disease agent. In exemplary aspects, the anti-Alzheimer's disease agent may be donepezil HCl, tacrine HCl, selegiline, lecithin, choline, physostigmine, L-deprenyl, arecoline, velnacrine maleate, vitamin E, estrogen, ampalex or acetyl-L-carnitine.

Also provided is a composition comprising a combined effective amount of R-ibuprofen and an anti-Alzheimer's disease agent. The composition may be dispersed in a pharmaceutically acceptable excipient. In another embodiment, the present invention provides a kit comprising, in suitable container means, R-ibuprofen and an anti-Alzheimer's disease agent.

In yet another aspect, the present invention provides a method of inhibiting protein kinase C in a cell, comprising contacting the cell with an amount of an R-ibuprofen composition effective to inhibit the protein kinase C in the cell. In an alternative embodiment, there is provided a method of inhibiting protein kinase C translocation into a membrane comprising contacting the cell with an amount of an R-ibuprofen composition effective to inhibit the translocation. In particular embodiments, the cell is a eukaryotic cell. In more particular embodiments, the tumor cell is selected from the group consisting of cecum, colon, rectum, jejunum, duodenum, esophagus, stomach, pancreas, liver, bile duct, gall bladder, prostate gland, breast, kidney, pituitary gland, adrenal gland, thyroid gland, ovary, testicle, lung, brain, bone, blood and bone marrow cell. In other aspects, the cell may be located within an animal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, FIG. 1B, FIG. 1C and FIG. 1D. Morphological changes and foci formation of NIH 3T3 cells exposed to PMA (0.02 µg/ml) and 2% FBS DMEM culture media for: FIG. 1A) 3 days, FIG. 1B) 8 days, FIG. 1C) 16 days, and FIG. 1D) 21 days. Cells exhibited multilayer growth at 3 days and foci formation at 8, 16 and 21 days of exposure, respectively. Slides were obtained by light microscopy (40× magnification).

FBS plus PMA 48 hr (PMA 48 hr.); 2% FBS plus PMA for 2 weeks (PMA 2 weeks). For SDS-PAGE, protein loading was 20 μg/lane. The 10% FBS nuclear lane was loaded with the corresponding cytosolic protein fraction to confirm the responsiveness of the nuclear preparation to PKCα detection.

Figure 4:
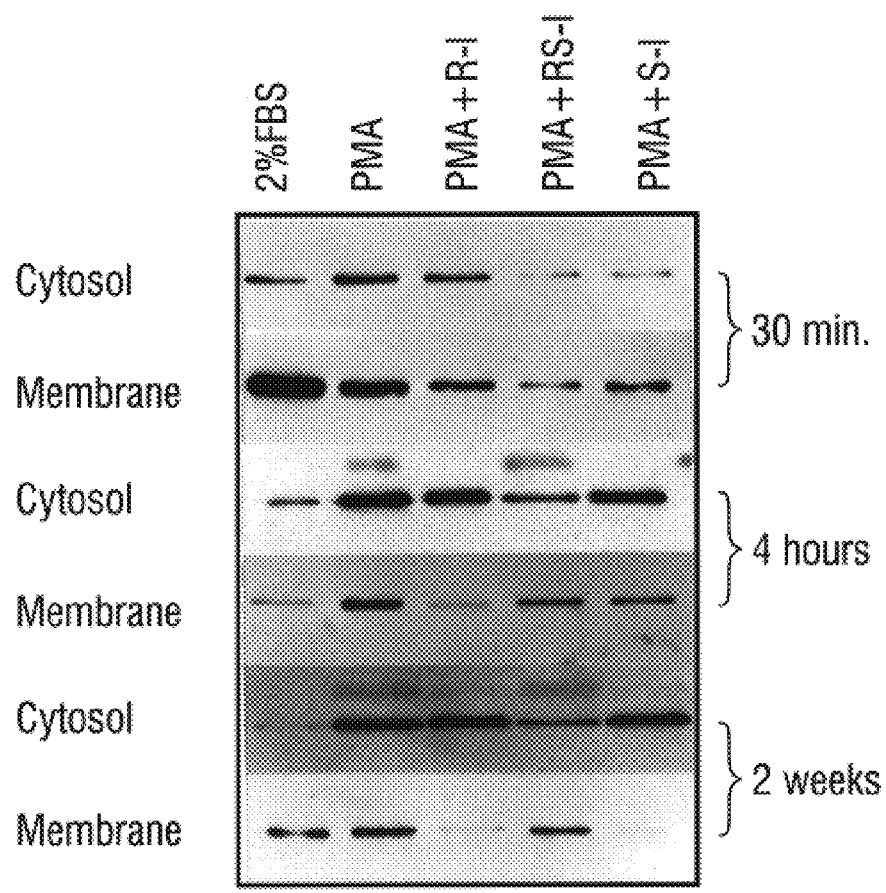

FIG. 4. Effects of R-ibuprofen (R-I), S-ibuprofen (S-I) and racemic ibuprofen (RS-I) on the time dependent translocation of PKCα from cytosol to membrane fractions. NIH 3T3 cells were cultured in 10% FBS to confluence and exposed for 30 min, 4 hr or 2 weeks to: 2% FBS (2% FBS); 2% FBS plus PMA (0.02 μg/ml) (PMA); 2% FBS, PMA and R-ibuprofen (10 μg/ml) (PMA+R-I); 2% FBS, PMA and racemic ibuprofen (10 μg/ml) (PMA+RS-I); 2% FBS, PMA and S-ibuprofen (10 μg/ml) (PMA+S-I). For SDS-PAGE, protein loading was 20 μg/lane. PKCα was not detected in the nuclear fraction of any ibuprofen treated group.

Figure 5:
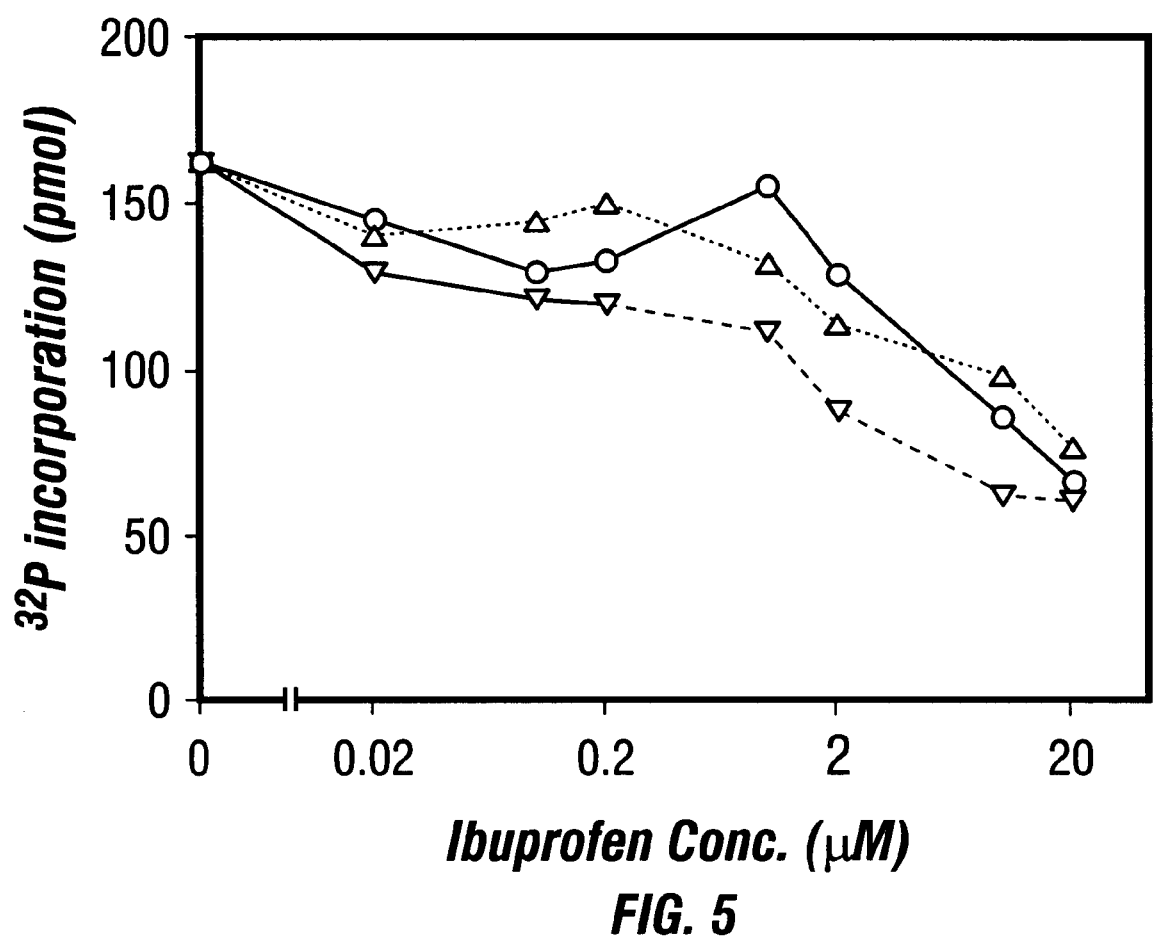

FIG. 5. Inhibition of PMA (32 nM; 0.02 μg/ml) stimulated PKC activity by racemic ibuprofen (○), R-ibuprofen (Δ) and S-ibuprofen(∇) using partially purified rat brain PKC. Histone phosphorylation was quantified as $^{32}P$ incorporation from 32P-γ-ATP at 30° C. for 2 min. Data are the mean of duplicate determinations.

Figure 6:
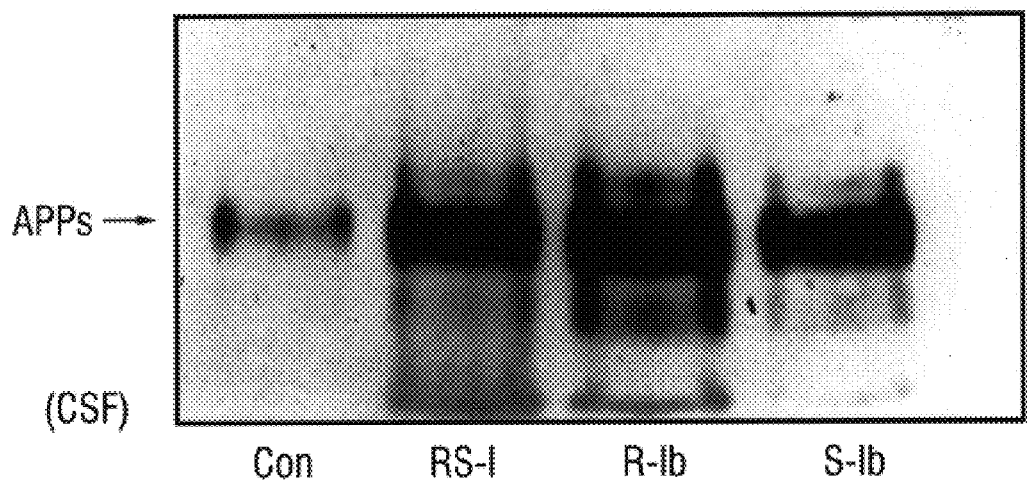

FIG. 6. Effect of Ibuprofen on rat cerebrospinal fluid APPs secretion.

Figure 7:
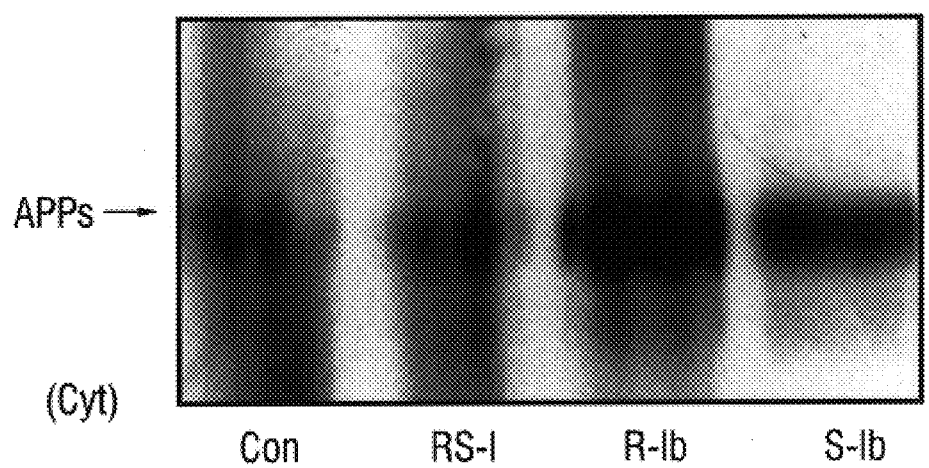

FIG. 7. Effect of Ibuprofen on rat brain cytosolic APPs content.

Figure 8:
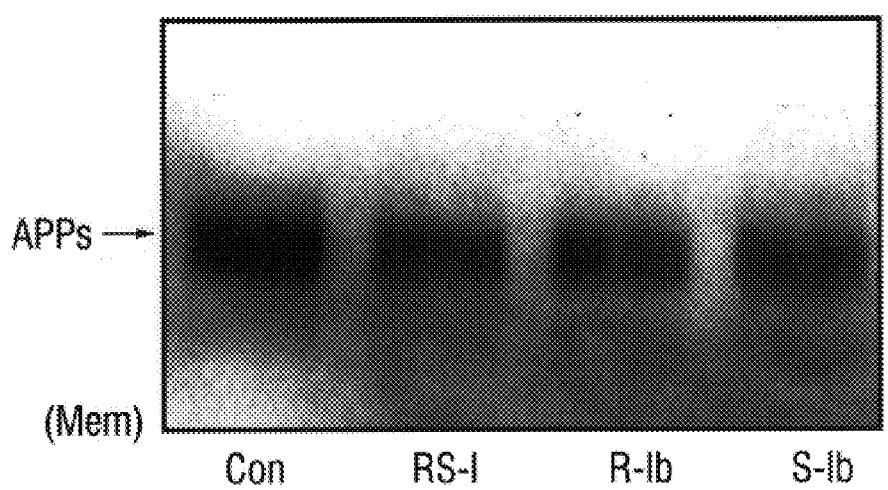

FIG. 8. Effect of Ibuprofen on rat brain membrane fraction APP content.

Figure 9:
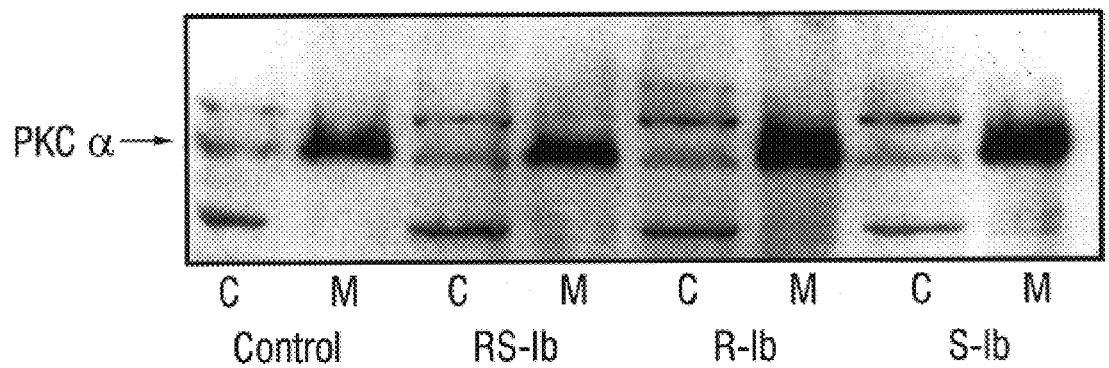

FIG. 9. Effect of Ibuprofen on PKCα content in rat brain cytosol (c) and membrane (m).

Figure 10:
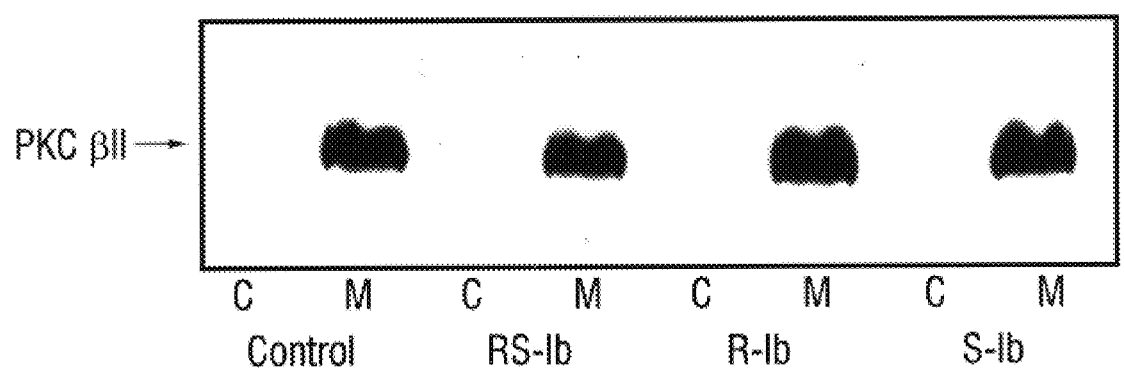

FIG. 10. Effect of Ibuprofen on PKC-βII content in rat brain cytosol (c) and membrane (m).

Figure 11:
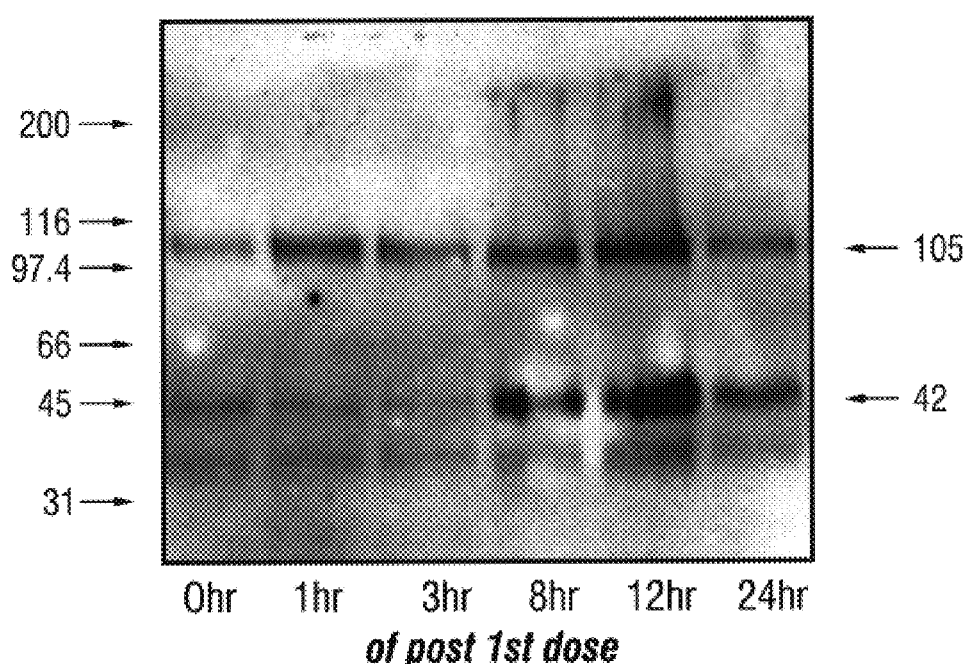

FIG. 11. The effect of racemic Ibuprofen on the time course of APPs in human serum following a single dose of 800 mg.

Figure 12:
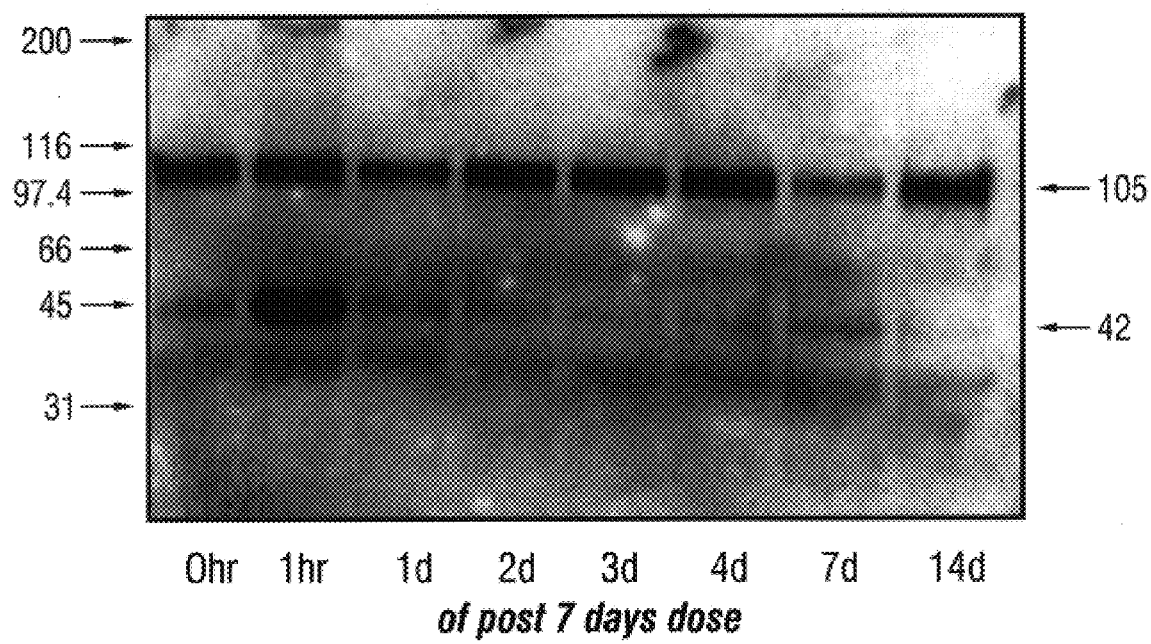

FIG. 12. The effect of racemic Ibuprofen on the time course of APPs in human serum following 7 days of treatment (800 mg t.i.d.)

Figure 13:
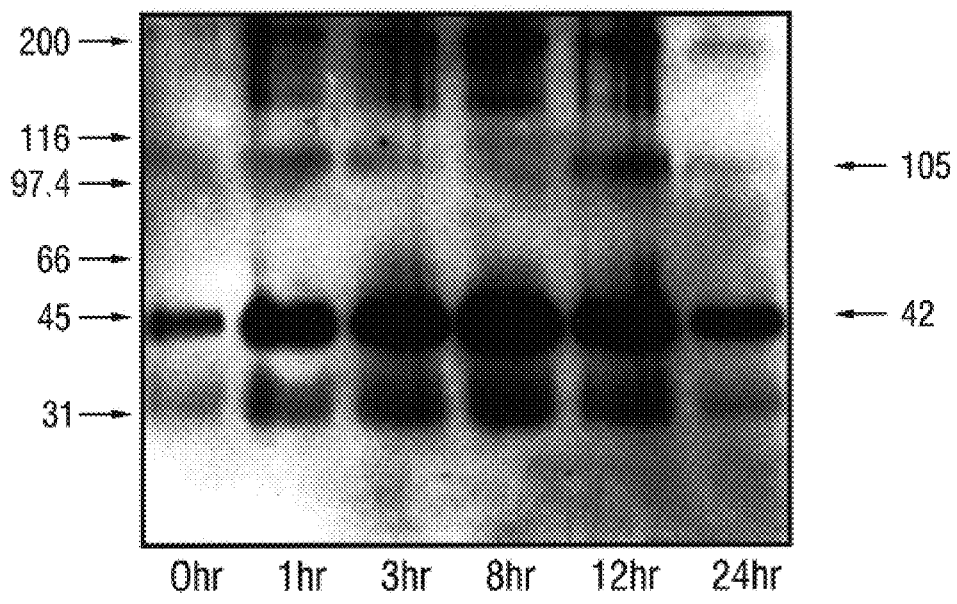

FIG. 13. The effect of S-ibuprofen on the time course of APPs in human serum following a single dose of 800 mg.

Figure 14:
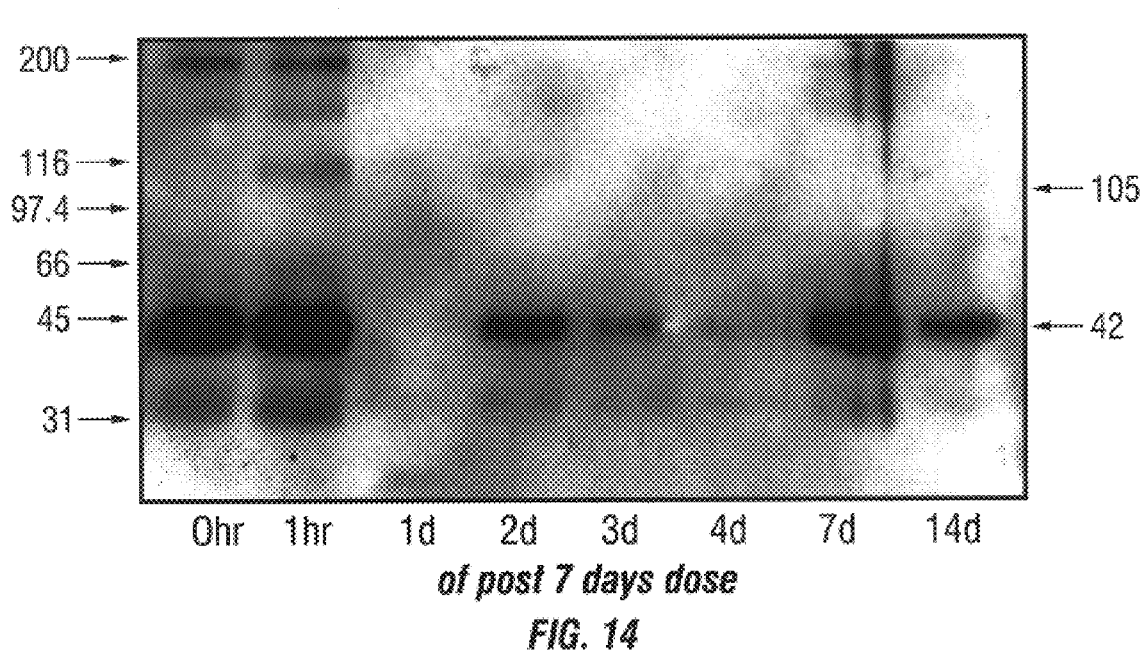

FIG. 14. The effect of S-ibuprofen on the time course of APPs in human serum following 7 days of treatment (800 mg t.i.d.)

DESCRIPTION OF ILLUSTRATIVE EMBODIMENTS

The present inventors have discovered that the R-enantiomer of ibuprofen is highly effective as a cancer therapeutic agent. Further the present invention describes the prophylactic and or therapeutic administration of the R-enantiomer of ibuprofen in patients exhibiting Alzheimer's disease and Alzheimer's associated disease. The details of the invention are described below.

1. Ibuprofen

A) Structure and Function

Ibuprofen, α-4-(2-methylpropyl) benzeneacetic acid, is a well known NSAID with anti-pyretic and analgesic properties. U.S. Pat. Nos. 3,228,831 and 3,385,886 described the structure and properties of ibuprofen and are specifically incorporated herein by reference. Commercially available ibuprofen is sold as a racemic mixture of an equal amount of the R and S enantiomers (see below). R- and S-ibuprofen are commercially available as pure enantiomers, with the S-enantiomer being the therapeutically active form in anal-gesic and anti-pyretic formulations (Caldwell et al., 1988; U.S. Pat. No. 4,851,444), being mediated by inhibition of cyclooxygenase activity.

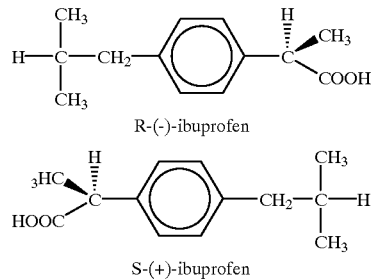

R-(-)-ibuprofen

S-(+)-ibuprofen

Ibuprofen is widely employed therapeutically for its antiinflammatory, analgesic and antipyretic properties that stem from the inhibition of cyclooxygenase activity. The latter properties are due principally to the S-enantiomer that is approximately 100 times more potent than R-ibuprofen in suppressing prostaglandin formation from arachidonic acid (Villanueva et al., 1993; Boneberg et al., 1996).

More recently, it has become clear that ibuprofen, in common with several other NSAIDs, has significant chemopreventitive activity. Ibuprofen, like other NSAIDs, inhibits the proliferation of human colon, lung, breast carcinoma and melanoma cell lines, such as Ht-29, A-427, MCF 7/s and UACC 375, respectively (Hixson et al., 1994) and has demonstrated anticancer activity in several animal cancer models, such as rat colon (Reddy et al., 1992) and mouse mammary glands (Metha et al., 1991), lung and gastric (Jabert and Castonguay, 1992) cancer induced by established carcinogens.

The inventors' results that show that in addition to racemic ibuprofen, both the R- and S-enantiomers inhibit the neoplastic transformation of NIH 3T3 cells induced by PMA. The latter is consistent with both R- and S-ibuprofen blocking the PKC dependent neutrophil respiratory burst induced by PMA in vitro (Bautista et al., 1992; Patterson et al., 1992).

In other case-control and cross sectional studies, evidence consistently supports the associations between use of non-steroidal anti-inflammatory drugs (NSAIDs) and lower risk of AD (Breitner et al., 1994; Breitner et al., 1995; Rich et al., 1995). In a double-blind, placebo-controlled, 6-month clinical trial, indomethacin was very effective in slowing AD progression (Rogers et al., 1993). Recently, in a longitudinal study, NSAIDs produced a 60% decrease in risk of AD with 2 or more years of use, but this was not associated with use of aspirin or acetaminophen (Stewart et al., 1997), which suggests anti-inflammatory effect of NSAIDs might not be a key function in slowing disease progression or prevention onset of AD.

Presently, the inventors have found that ibuprofen, particularly the R-enantiomer, can form ibuprofen-diacylglycerol (Ib-DAG) which activates PKC in vitro and is consistent with the activation of PKC in vivo (Xiaotao et al., 1996). The inventors have now demonstrated that ibuprofen increases APPs secretion to prevent onset and slow progression of AD. Further the present invention shows that R-ibuprofen is more effective than S-ibuprofen and racemic ibuprofen, and causes less gastropathy because of its very weak capability to inhibit cyclooxygenase.

Thus, the present invention demonstrates that, contrary to the teaching of the prior art, the R-isomer of ibuprofen is an effective therapeutic agent. In a particular aspect of the present invention, the R-isomer of ibuprofen is provided to inhibit neoplastic transformation of mammalian cells, thereby causing a chemopreventive effect in said cells. In certain aspects, it is suggested that the R-ibuprofen is administered alone or in combination with conventional chemotherapeutic agents as described herein below. R-ibuprofen has been shown by the present inventors to inhibit protein kinase C activation in cells. Moreover, the present invention demonstrates that R-ibuprofen may be prophylactically and/or therapeutically administered to a subject having or suspected of having Alzheimer's or Alzheimer's-related diseases. Methods and compositions of making and using R-ibuprofen in relation to these aspects of the invention are described in further detail herein below.

B) Purification from Racemic mixture

R- and S-ibuprofen are commercially available as pure enantiomers or as racemic ibuprofen which is an equal mixture of R- and S-ibuprofen. Racemic ibuprofen can be obtained from Sigma Chemical Co., St. Louis, MO. Pure R- or S-ibuprofen can be obtained from Research Biochemicals International, Natick, Mass.

There are numerous processes for the separation of S-ibuprofen from R-ibuprofen known to those of skill in the art. Most such processes rely on the resolution of the two isomers, the skilled artisan is referred to U.S. Pat. No. 5,621,140 for detailed description of the resolution of ibuprofen using N-alkyl-D glucamine as a resolving agent. In resolving the two isomers, it will be possible to produce a racemically enriched R-ibuprofen composition. An "R-ibuprofen composition" as used herein is a composition comprising enantiomerically enriched R-ibuprofen, R-ibuprofen substantially free from S-ibuprofen, or a substantially pure R-ibuprofen isomer. By racemically enriched it is meant that the composition is at least 90% R-ibuprofen, in more preferred embodiments the composition comprises at least 92% R-ibuprofen, 94% R-ibuprofen, 96% R-ibuprofen, 98% ibuprofen, with compositions comprising 99% and 100% R-ibuprofen being most preferred.

In certain other applications, (S)-α-methylbenzylamine has been employed as a resolving agent (Kaiser et al., 1976). U.S. Pat. No. 4,209,638 discloses a process for enriching a desired enantiomer from racemic arylpropionic acids by partial dissolution resolution technique. Lukas et al., (U.S. Pat. No. 4,983,765) disclose a separation process in which the reaction to a diastereomeric salt takes place in a polar solvent, and the salt is purified by several crystallizations to produce an optically pure material. Alternatively, it is possible to react the racemic mixture with an organic or inorganic acid to form a salt solution. The salt solution is then reacted with a chiral base such as (S)-α-methylbenzylamine to precipitate the less soluble diastereomeric salt from the reaction mixture (U.S. Pat. No. 5,015,764). Other methods for resolving a racemic mixture are disclosed in U.S. Pat. Nos. 4,994,604; 5,332,8344, 246,164; 4, 246,193; 4,515,811 and 4,501,727.

As an alternative source of pure R- and S-ibuprofen, it is possible to start with racemic ibuprofen and resolve the enantiomers using the following chiral high performance liquid chromatography procedure previously described for resolving the enantiomers of ketoprofen (Grubb et al., 1996). The HPLC column consists of a 5 $\mu$m (S,S)-Wlhelk-O1 stationary phase (250 mm×4.6 mm; Regis Technologies, Morton Grove, Ill.) and may be eluted using for example, a mobile phase of hexane/isopropyl alcohol/acetic acid (98/2/0.05) flowing at 0.8 ml/min. R- and S-ibuprofen are eluted at 13 and 16 min. respectively. Quantitation may be achieved using peak area ratios with R-flurbiprofen as internal standard and ultraviolet absorbance at 254 nm. The limit of quantitation can be predetermined and set at, for example, set at 100 ng/ml. Similarly it will be possible to separate the racemic mixture into the individual isomers using thin layer chromatography, using a similar mobile phase to that used for HPLC.

C) Therapeutic Doses of R-Ibuprofen

Ibuprofen is well absorbed orally from suspensions, drops, caplets and chewable tablet formulations (see below). Like most drugs of its kind ibuprofen is highly protein bound. Protein binding is saturable and at concentrations >20 $\mu$g/ml binding is non-linear. After oral administration the majority of the dose is recovered in the urine within 24 hours as the hydroxy-(25%) and carboxypropyl-(37%) phenylpropionic acid metabolites It is contemplated that the dosages of ibuprofen currently used in analgesics and anti-pyretic applications of S-ibuprofen will provide a guideline for administration of R-ibuprofen as an antineoplastic agent and as an agent for combating Alzheimer's disease and other age related dementias.

As such it is contemplated that doses of 50, 100, 200, 400, 600, 800, 1200, 1600, 3200 3500, 4000 mg per day will be useful in the therapeutic applications of the present invention. Such doses may be administered in a single administration or may be administered over a variety of time intervals during a particular treatment regimen. 2. Ibuprofen and Cancer There is clear evidence from both prospective and retrospective clinical studies that exposure to non-steroidal anti-inflammatory drugs (NSAIDs), such as ibuprofen, aspirin, indomethacin, sulindac and piroxicam, reduces the risk of certain human cancers (Turner and Berkel, 1993; Heath et al., 1994; Giovannucci et al., 1995). In particular, large bowel cancer associated with familial polyposis is 2-fold less prevalent in chronic NSAID users (Giovannucci et al., 1995). The obligatory inhibition of cyclooxygenase associated with NSAIDs has been proposed as the mechanism by which they exert their chemopreventitive effects and therefore determines the strategy for identifying drugs with a greater therapeutic index than those currently employed. It has been suggested that NSAIDs inhibit the activity of inducible cyclooxygenase-2 perhaps combined with inhibition of ornithine decarboxylase activity, and that the resulting reduction of prostaglandin and/or polyamine biosynthesis inhibits tumor promotion and carcinogenesis (Heath et al., 1994; Marnett et al., 1992; Love et al., 1992).

However, such hypotheses have not been rigorously evaluated and it remains possible that non-cyclooxygenase dependent pathways contribute to NSAID chemopreventitive properties. Examples of such properties include the inhibition of phospholipase C activity (Bomalaski et al., 1986), uncoupling of G-protein mediated signaling (Abramson et al., 1991) and the inhibition of NF-κB translocation to the nucleus (Kopp, and Ghosh, 1994). Interestingly, ibuprofen blocks neutrophil activation by chemotactic agents but this effect is not enantioselective despite the fact that inhibition of cyclooxygenase activity by ibuprofen resides almost exclusively in the S-enantiomer (Villanueva et al., 1993).

The NIH 3T3 cell line is one of the most widely used and best characterized model for determining the transforming potential of particular genes such as those associated with ras oncogene sequences (Dotto et al., 1985; Bishop et al., 1987). These cells undergo neoplastic transformations without the requirement for exogenous oncogenes in a manner that depends on the environment (Rubin, and Xu, 1989;

Rubin et al., 1990). In particular, at high cell densities and low culture fetal bovine serum (2%) exposure to PMA induces NIH 3T3 cells to form foci and become tumorigenic in a manner analogous to spontaneous neoplastic transformation by providing a milieu that encourages selection of the transformed phenotype (Bishop et al., 1987; Rubin and Rubin, 1994). Phorbol esters such as PMA are promoters of skin tumor formation (Castagna et al., 1982) and directly activate PKCs (Driedger and Blumberg, 1977) which are believed to be the high affinity PMA receptor for tumor promotion (Neidel et al., 1983); PMA also transiently induces c-jun expression in NIH 3T3 cells (Lamph et al., 1988). Therefore, in view of the central role that PKC plays in carcinogenesis and the neoplastic transformation of cultured cells, such as NIH 3T3 cells, the inventors have used this model in vitro to study the chemopreventitive potential of ibuprofen and to examine the associated changes in PKC regulation. In particular, the inventors directly examined the hypothesis that cyclooxygenase inhibition is obligatory for ibuprofen to exhibit chemopreventitive properties by comparing the cyclooxygenase inhibiting S-ibuprofen to its noninhibitory optical antipode.

The influence of R-, S- and racemic ibuprofen on the neoplastic transformation and corresponding intracellular localization of protein kinase $C\alpha$ (PKC$\alpha$) was examined in NIH 3T3 cells treated with phorbol 12-myristate 13-acetate (PMA). In control cells, decreasing fetal bovine serum (FBS) media content from 10% to 2% resulted in PKC$\alpha$ translocation from cytosol to membrane but not to the nuclear fraction and no significant neoplastic transformation occurred in 6 weeks of culture. After 4 to 18 hours of culture with reduced media FBS plus PMA (0.02 $\mu$g/ml) there was significant translocation of PKC$\alpha$ to both nuclear and microsomal membranes; under these conditions, 2 to 6 weeks of culture resulted in neoplastic transformation and translocation of PKC$\alpha$ to the membrane sites. R-ibuprofen, S-ibuprofen and the racemate substantially inhibited the neoplastic transformation produced by low media FBS and PMA. Ibuprofen protection against neoplasm corresponded to an inhibition of PKC$\alpha$ translocation to nuclear and microsomal membranes. R- and S-ibuprofen were more effective than the racemic mixture in suppressing neoplastic transformation and PKC$\alpha$ translocation from cytosol to membrane after 2 weeks of PMA exposure. Inversion of R-ibuprofen to S-ibuprofen did not occur. Direct inhibition of PKC-mediated phosphorylation by R-, S-, and racemic ibuprofen was modest ($\approx$60%). The R- and S-enantiomers displayed superior chemopreventitive effects relative to racemic ibuprofen suggesting that mechanisms other than cyclooxygenase inhibition contribute to the chemopreventitive properties of at least some NSAIDs.

A) Types of Cancer

The present invention involves, in one embodiment, the treatment of cancer. The types of cancer that may be treated, according to the present invention, is limited only by the involvement of PKC$\alpha$. In particular, ibuprofen protection against neoplasm corresponds to an inhibition PKC$\alpha$ translocation to nuclear and microsomal membranes. Thus, it is contemplated that a wide variety of tumors may be treated using R-ibuprofen, including cancers of the cecum, colon, rectum, jejunum, duodenum, esophagus, stomach, pancreas, liver, bile ducts, gall bladder, prostate gland, breast, kidney, pituitary gland, adrenal gland, thyroid gland, ovary, testicle, lung, brain, bone, blood, bone marrow and other tissues.

In many contexts, it is not necessary that the tumor cell be killed or induced to undergo normal cell death or "apoptosis." Rather, to accomplish a meaningful treatment, all that is required is that the tumor growth be slowed or metastasis inhibited to some degree. It may be that the tumor growth is completely blocked, however, or that some tumor regression is achieved. Clinical terminology such as "remission" and "reduction of tumor" burden also are contemplated given their normal usage.

B) Anti-Cancer Drugs

A wide variety of chemotherapeutic agents may be used in combination with the ibuprofen compositions of the present invention. These can be, for example, agents that directly cross-link DNA, agents that intercalate into DNA, and agents that lead to chromosomal and mitotic aberrations by affecting nucleic acid synthesis.

Agents that damage DNA also include compounds that interfere with DNA replication, mitosis, and chromosomal segregation. Examples of these compounds include adriamycin (also known as doxorubicin), VP-16 (also known as etoposide), and the like. Widely used in clinical setting for the treatment of neoplasms these compounds are administered through bolus injections intravenously at doses ranging from 25–75 mg/m$^2$ at 21 day intervals for adriamycin, to 35–100 mg/m$^2$ for etoposide intravenously or orally.

Doxorubicin hydrochloride, 5,12-Naphthacenedione, (8s-cis)-10-[(3-amino-2,3,6-trideoxy-a-L-lyxo-hexopyranosyl) oxy]-7,8,9,10-tetrahydro-6,8,11 trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Daunorubicin hydrochloride, 5,12-Naphthacenedione, (8S-cis)-8-acetyl-10-[(3-amino-2,3,6-trideoxy-α-L-lyxo-hexanopyranosyl)oxy]-7,8,9,10-tetrahydro-6,8,11-trihydroxy-10-methoxy-, hydrochloride; also termed cerubidine and available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs, it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m²/day (30 mg/m² for patients older than 60 yr.) for 1, 2 or 3 days every 3 or 4 wk or 0.8 mg/kg/day for 3 to 6 days every 3 or 4 wk; no more than 550 mg/m² should be given in a lifetime, except only 450 mg/m² if there has been chest irradiation; children, 25 mg/m² once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m², 20 mg/m², 30 mg/m², 50 mg/m², 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Mitomycin (also known as mutamycin and/or mitomycin-C) is an antibiotic isolated from the broth of Streptomyces caespitosus which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced crosslinking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg., 20 mg., or 10 mg. I.V., the maximal serum concentrations were 2.4 mg./mL, 1.7 mg./mL, and 0.52 mg./mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Bleomycin is a mixture of cytotoxic glycopeptide antibiotics isolated from a strain of Streptomyces verticillus. It is freely soluble in water. Although the exact mechanism of action of bleomycin is unknown, available evidence would seem to indicate that the main mode of action is the inhibition of DNA synthesis with some evidence of lesser inhibition of RNA and protein synthesis.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed. Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted. Bleomycin may be given by the intramuscular, intravenous, or subcutaneous routes.

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15–20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg/m$^2$. Of course, all of these dosages are exemplary, and any dosage in-between these points is also expected to be of use in the invention.

Cisplatin is not absorbed orally and must therefore be delivered via injection intravenously, subcutaneously, intra-tumorally or intraperitoneally.

VP 16 is also know as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200–250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

Tumor Necrosis Factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α so has been found to possess anti-cancer activity.

Taxol is an experimental antimitotic agent, isolated from the bark of the ash tree, Taxus brevifolia. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/$mm^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 $mg/m^2$ can also be administered. Alternatively, 0.1 $mg/m^2$, 0.12 $mg/m^2$, 0.14 $mg/m^2$, 0.15 $mg/m^2$, 0.2 $mg/m^2$, 0.25 $mg/m^2$, 0.5 $mg/m^2$, 1.0 $mg/m^2$, 1.2 $mg/m^2$, 1.4 $mg/m^2$, 1.5 $mg/m^2$, 2.0 $mg/m^2$, 2.5 $mg/m^2$, 5.0 $mg/m^2$, 6 $mg/m^2$, 8 $mg/m^2$, 9 $mg/m^2$, 10 $mg/m^2$, 20 $mg/m^2$, can be given. Of course, all of these dosages are exemplary, and any dosage in-between these points is also expected to be of use in the invention.

Carmustine (sterile carmustine) is one of the nitrosoureas used in the treatment of certain neoplastic diseases. It is 1,3-bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 $mg/m^2$ intravenously every 6 weeks. This may be given as a single dose or divided into daily injections such as 75 to 100 $mg/m^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 $mg/m^2$, 20 $mg/m^2$, 30 $mg/m^2$ 40 $mg/m^2$ 50 $mg/m^2$, 60 $mg/m^2$, 70 $mg/m^2$, 80 $mg/m^2$, 90 $mg/m^2$, 100 $mg/m^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject.

Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a $pKa_1$ of ~2.1. Melphalan is available in tablet form for oral administration and has been used to treat multiple myeloma.

Available evidence suggests that about one third to one half of the patients with multiple myeloma show a favorable response to oral administration of the drug. Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject.

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [$(ClCH_2CH_2)_2N$—$POCl_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day . A dose 250 mg/kg/day may be administered as an antineoplastic. Because of gastrointestinal adverse effects, the intravenous route is preferred for loading. During maintenance, a leukocyte count of 3000 to 4000/ mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

Chlorambucil (also known as leukeran) was first synthesized by Everett et al. (1953). It is a bifunctional alkylating agent of the nitrogen mustard type that has been found active against selected human neoplastic diseases. Chlorambucil is known chemically as 4-[bis(2-chlorethyl)amino] benzenebutanoic acid.

Chlorambucil is available in tablet form for oral administration. It is rapidly and completely absorbed from the gastrointestinal tract. After single oral doses of 0.6–1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan (also known as myleran) is a bifunctional alkylating agent. Busulfan is known chemically as 1,4-butanediol dimethanesulfonate, but is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours. The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m$^2$ as a single oral dose every 6 weeks. In individuals with compromised bone marrow function, the dose should be reduced to 100 mg/m$^2$ every 6 weeks. When lomustine is used in combination with other myelosuppressive drugs, the doses should be adjusted accordingly. It is understood that other doses may be used for example, 20 mg/m$^2$ 30 mg/m$^2$, 40 mg/m$^2$, 50 mg/m$^2$,60 mg/m$^2$,70 mg/m$^2$,80 mg/m$^2$,90 mg/m$^2$, 100 mg/m$^2$, 120 mg/m$^2$ or any doses between these figures as determined by the clinician to be necessary for the individual being treated.

TABLE 1

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE* |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) | Multiple myeloma, breast, ovary |

TABLE 1-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE* |
|---|---|---|---|
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidazole carboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Anologs | Fluouracil (5-fluorouracil; 5-FU) | Breast, colon, stomach, pancreas, ovary, head and neck, urinary bladder, premalignant skin lesions (topical) |
| | | Floxuridine (fluorode-oxyuridine; FUdR) | |
| | | Cytarabine (cytosine arabinoside) | Acute granulocytic and acute lymphocytic leukemias |
| | Purine Anologs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide | Testis, small-cell lung and other lung, breast, Hodgkin's disease, non-Hodgkin's lymphomas, acute granulocytic leukemia, Kaposi's sarcoma |
| | | Tertiposide | |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia, Kaposi's sarcoma, melanoma, carcinoid, |

TABLE 1-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE* |
|---|---|---|---|
| Miscellaneous Agents | Platinum Coordination Complexes | Cisplatin (cis-DDP) Carboplatin | renal cell, ovary, bladder, non-Hodgkin's lymphomas, mycosis fungoides, multiple myeloma, chronic granulocytic leukemia Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) Aminoglutethimide | Adrenal cortex Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadatropin-releasing hormone analog | Leuprolide | Prostate |

Exemplary chemotherapeutic agents that are useful in connection with combined therapy are listed in Table 1. Each of the agents listed therein are exemplary and by no means limiting. The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

C) Combined Therapeutics

The administration of R-ibuprofen to tumor cells may augment the response of those cells to other kinds of cancer therapy. The mechanism by which this phenomenon occurs are not well established, but in view of the central role that PKC plays in carcinogenesis and the neoplastic transformation of cells, the inventors suggest that inhibition of PKCα activity by ibuprofen as shown herein, will be beneficial in the treatment of tumors.

Agents or factors suitable for use in a combined therapy include radiation and waves that induce DNA damage such as γ-irradiation and X-rays and the like. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In addition to chemo- and radiotherapies, it also is contemplated that combination with gene therapies will be advantageous. For example, Rb, p53 and p16 are powerful tumor suppressors that can be used effectively as therapeutics. Any other tumor-related gene (tumor suppressor or antisense oncogene) conceivably can be utilized in this manner, for example, p21, APC, DCC, NF-1, NF-2, BCRA2, p16, FHIT, WT-1, MEN-1, MEN-II, BRCA1, VHL, FCC, MCC, ras, myc, neu, raf erb, src, fins, jun, trk, fos, ret, gsp, hst, bcl and abl, using either a sense or antisense approach.

The inventors propose that the systemic delivery of the R-ibuprofen and/or the secondary agent will be an appropriate method to achieve the required therapeutic dosages to a diseased state. Alternatively, regional delivery of R-ibuprofen to patients will be a very efficient method for delivering a therapeutically effective composition to counteract the clinical disease. Similarly, the chemo- or radiotherapy may be directed to a locally or regionally to a particularly affected part of the subject's body.

These compositions all would be provided in a combined amount effective to abrogate the growth of the diseased cell.

This process may involve contacting the cells with the R-ibuprofen and other factor(s) at the same time. This may be achieved by contacting the cell with a single composition or pharmacological formulation that includes both, or by contacting the cell with two distinct compositions or formulations, at the same time, wherein one composition includes the R-ibuprofen formulation and the other composition includes the second agent.

Alternatively, the R-ibuprofen treatment may precede or follow the other agent treatment by intervals ranging from minutes to weeks. In embodiments where the second agent and R-ibuprofen therapy are applied separately to the cell, one would generally ensure that a significant period of time did not expire between the time of each delivery, such that the agents would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the R-ibuprofen or the other agent will be desired. Various combinations may be employed, where R-ibuprofen is "A" and the other agent is "B", as exemplified below:

A/B/A B/A/B B/B/A A/A/B B/A/A A/B/B B/B/B/A B/B/ A/B

A/A/B/B A/B/A/B A/BIB/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve induction of cell death, both agents are delivered to a cell in a combined amount effective to induce apoptosis.

3. Ibuprofen and Alzheimer's Disease

Alzheimer's disease is characterized by neuronal dysfunction and depositions of amyloid β-protein (Aβ) in the form of intracellular neurofibrillary tangles, extracellular plaques, and cerebrovascular amyloid which causes degeneration of synapses and neurons (Masters et al., 1985; Price et al., 1992). Aβ, a self-aggregating protein that consists of a 39–43 amino acid peptide, is generated by enzymatic proteolytic processing of amyloid precursor protein (APP) (Robakis et al., 1987; Goldegraber et al., 1987; Tangi et al., 1988). In normal brain APP is degraded (between amino acids Lysine 16 and Leucine 17) by "α-secretase" and a 90–100 kD soluble non-amyloidogenic NH2-terminal fragment of APP (APPs) is secreted from the cells; AP is not generated from this process (Anderson et al., 1991; Sisodia et al., 1990; Esch et al., 1990). In the brain of AD patients, PKC ax and ,II are significantly decreased.

The metabolism of APP is highly regulated by protein kinase C (PKC). PKC expression extremely low in AD brain (Cole et al., 1988), and consists predominantly of PKC-α, β, and ε. PKC alteration in neurons is an early biochemical marker in AD (Shimohama et al., 1993; Matsushima et al., 1996; Mashiah et al., 1991). The activation of PKC by a phorbol ester can increase the formation of APPs and reduce the production of amyloidogenic fragments containing Aβ and Aβ itself (Caporaso et al., 1990; Slack et al., 1993). The target protein for phosphorylation by PKC could be a-secretase or coating proteins in the trafficking vesicles containing APP.

The present invention shows that the R-enantiomer of ibuprofen, can form ibuprofen-diacylglycerol (Ib-DAG) which activates PKC in vitro and is consistent with the activation of PKC in vivo (Xiaotao et al., 1996). Ibuprofen increases APPs secretion to prevent onset and slow progression of AD. The capability of ibuprofen to increase APPs secretion from brain may reflect the activation of rat brain PKCs. Further, the present invention shows that R-ibuprofen is more effective than S-ibuprofen and racemic ibuprofen and cause less gastropathy because of its very weak capability to inhibit cyclooxygenase.

The present invention provides compositions of R-ibuprofen for the treatment of Alzheimer's disease. Other diseases related to Alzheimer's may also be treated by the present compositions. Such diseases include but are not limited to Alzheimer's related disease; Amyloid disease, amyloid related disease, amyloid related dementia Alzheimer's related dementia, aging associated amyloid disorder, aging associated dementia. These dementia are generally age-related.

B) Monitoring Efficacy of Treatment

It is envisioned that prior to administering the ibuprofen compositions to a human subject it may be necessary to test efficacy of the treatment in animal models to determine the exact dosages and time intervals required for effective treatment. There are available a wealth of animal models that may be useful for the evaluation of R-ibuprofen as an effective treatment in mammals.

Certain kinds of memory have been successfully modeled. It is relatively easy to show that an animal can learn to execute a particular response, for example a lever press or the pathway to a particular goal in a maze and then study the forgetting of this learned response after a period of time. This type of memory is long term memory. The alternative is working memory and can be tested by subjecting the animal to a behavioral task that requires the animal to retain the information for very short periods, e.g., in which branches of a radial maze it has already found food in and does not need to visit. The working memory function is the type of memory function most often impaired by aging in animals and humans. The forgetting of a particular response can be enhanced in an animal model by various experimental procedures including administering amnesia inducing agents, brain lesions, hypoxia or by using aged animals. These procedures have often served for the evaluation of potential cognition enhancing agents. The test most often used for the reasonably rapid screening of compounds is the passive avoidance test, other tests include 17-arm radial maze, Lashley III maze, and one-way active avoidance testing (Socci et al., 1995).

The 17-arm radial maze is a highly complex spatial task that allows the determination of general learning, reference memory (long term) and working memory and is described in detail by Socci et al., (1995). Similar experiments can be performed in humans, for example, the working memory (WM) capacity of humans were with a 17-arm radial maze and, in a follow up experiment, with a 13-arm radial maze by Glassman et al., (1994). Both mazes were 15.2 meters in diameter, painted on a grassy field. In one version of the 13-arm experiment, a concurrent nonsense vocalization was required to impede subjects' use of language to remember locations. Subjects were instructed to choose arms of the radial maze unsystematically, as rats generally appear to do and to visit the end of each arm only once. In additional procedures, working memory capacity can be tested in a verbal task that is more analogous to the radial maze than is the typical ordered recall test for example, subjects are asked to try to recite a sequence of 17 numbers (i.e., 18 through 34) or letters (A through Q) in unsystematic order, with no repeats. In another experiment subjects recited 13 numbers (14–26) or letters (A–M). The use of such tests prior to and concurrently with the administration of the therapeutic compositions of the present invention will allow the determination of efficacy of the R-ibuprofen as an effective drug against memory impairment associated with Alzheimer's and Alzheimer's related diseases.

Alternatively, the APP secretion may be monitored with any increase in APP secretion being indicative of the ibuprofen having a beneficial effect as described herein above.

C) Anti-Alzheimer's Drugs

At present there are no drugs in the United States that are recognized to be clearly effective in the treatment of age-related mental decline. Nevertheless, there are several promising drugs available in other parts of the world that have a limited efficacy. One such drug Hydergin® (codergocrine rriesyiate) is an FDA approved drug that has this indication. Other compounds that may prove useful, are priacetam, meclophenoxate, naftidrofuryl, ginkgo biloba, donepezil HCl, tacrine HCl, selegiline, lecithin, choline, physostigmine, L-deprenyl, arecoline, velnacrine maleate, vitamin E, estrogen, ampalax, vincamine and cyclandelate.

Dementia is a generic term referring to a syndrome of declining cognitive function. The clinical course of disorder is extremely variable and the causes are thought to be variable. About 70% of progressive dementia are believed to be caused in part by Alzheimer's disease (Rosser, 1993). The pathophysiology of Alzheimer's disease involves structural disease of the cerebrum and diencephalon. The degeneration and loss of nerve cells with secondary changes in cerebral white matter, with Alzheimer's disease being characterized by neurofibrillary tangles and senile plaques on the hippocampus and cortex. The underlying etiology of is often undetectable however, the dementia and the underlying lesions are often attributable to identifiable disorders such as hydrocephlus, syphilis and certain viral infections. Thus the disease may be due to a variety of disorders, many of which are treatable. Therefore, it is envisioned that the R-ibuprofen therapeutic compositions of the present invention may be administered alone or in combination with such treatments.

In this context, it will be necessary to monitor the patient for a decrease in signs and symptoms of dementia. Such signs and symptoms include irritability, lack of interest, distractibility, unclear thinking, loss of memory and wide mood swings in the early stages of the disorder. In more progressed cases the diseases is characterized by incontinence, aphasia and speech disorders. Thus in the therapeutic administration of ibuprofen to the patient, any decrease or alleviation in such symptoms of dementia will be considered as beneficial.

In the alternative, it has been shown that Alzheimer's Disease is often familial. Thus in those individuals form families known to have a history of the disease it would be beneficial to administer ibuprofen prophylactically. This is especially advantageous given the present findings that the R-enantiomer of ibuprofen is not associated with gastropathy or any other known adverse conditions.

As discussed herein the therapeutic formulations of ibuprofen may be in the form of tablets, caplets, suspensions, powders, drops or any other formulations commonly used in preparation of ibuprofen as an analgesic. The doses of the drug may be administered hourly, daily or weekly at time determined by the physician.

4. Formulations and Routes for Administration to Patients

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

The agents can be administered orally, intravenously, intramuscularly, intrapleurally or intraperitoneally at doses based on the body weight and degree of disease progression of the patient, and may be given in one, two or even four daily administrations.

One will generally desire to employ appropriate salts and buffers to render agents stable and allow for uptake by target cells. Aqueous compositions of the present invention comprise an effective amount of the agent, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and anti-fungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. Transdermal devices are well known to those of skill in the art and are described in U.S. Pat. Nos. 3,742,951; 3,797,494; 3,996,934 and 4,031,894.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the compositions of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including gels, pastes, powders and slurries. The active ingredient may be added in a therapeutically effective amount to a paste dentifrice that may include water, binders, abrasives, flavoring agents, foaming agents, and humectants.

In a particularly preferred embodiment, the R-ibuprofen compositions of the present invention are formulated in tablets for use as oral drugs. U.S. Pat. Nos 5,087,454 and 4,904,477 describe the compression of ibuprofen into tablet form, these patents are incorporated herein by reference in order to teach how to make compressed tablets and caplets.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

5. Kits

All the essential materials and reagents required for inhibiting tumor cell proliferation or for treating Alzheimer's and Alzheimer's-related diseases with the compositions of the present invention may be assembled together in a kit. When the components of the kit are provided in one or more liquid solutions, the liquid solution preferably is an aqueous solution, with a sterile aqueous solution being particularly preferred.

For in vivo use, an R-ibuprofen formulation, alone or in combination with a chemotherapeutic agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of these kits may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the R-ibuprofen and/or the chemotherapeutic drug, or explaining the assays for determining APPs levels in Alzheimer's patients.

The kits of the present invention also will typically include a means for containing the vials in close confinement for commercial sale such as, e.g., injection or blow molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

6. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Experimental Procedures

Materials:

(−)-R-ibuprofen and (+)-S-ibuprofen (optical purity >99%) were obtained from Sepracor Inc. (Marlborough, Mass.). The following were obtained from the Sigma Chemical Co. (St. Louis, Mo.): racemic ibuprofen, Dulbecco's modified Eagle's medium (DMEM), fetal bovine serum (FBS), histone, phosphatidyl serine and phorbol 12-myristate 13-acetate (PMA). Anti-PKCα antibody (affinity purified) and its C-terminal region peptide was obtained from Life Technologies (Gaithersburg, Md.). Partially purified PKCα from rat brain (>90% PKCα based on 82 kD protein band by Western blot) was obtained from Promega (Madison, Wis.). All other chemicals were of the highest available purity and were obtained from standard commercial sources.

Cell Culture:

NIH 3T3 cells (American Type Culture Collection, Rockville, Md.) were cultured in DMEM supplemented with 10% FBS inoculated at $10^4$ cells/35 cm dish. After reaching confluence, the cells were randomly divided into the following groups; control (0.01% DMSO), PMA (0.02 μg/ml (32 nM) in DMSO 0.01%;), PMA (32 nM) plus R-, S- or racemic ibuprofen (10 or 100 μg/ml, i.e. 49 μM or 490 μM). PMA and ibuprofen were dissolved in DMSO and stored in 5% DMSO stock solutions that were diluted a 1000-fold with culture media prior to use. Studies were initiated with control or ibuprofen treatment for 24 hours in DMEM with 10% FBS followed by DMEM with 2% FBS, PMA and ibuprofen as indicated for the stationary maintenance cultures. The media containing freshly added PMA and ibuprofen were changed every 60 hours for both the foci formation assay and PKCα analysis by Western blot.

Foci Formation Assay:

The focus formation capability of each treatment was measured by the method of Rubin (Rubin and Rubin, 1994). Briefly, the cells were cultured for 6 week in DMEM containing 2% FBS with PMA and ibuprofen (10 or 100 μg/ml; 49 or 485 μM), and then fixed with Bouin's reagent (Sigma Chemicals). Subsequent to washing with a tris/saline buffer, the cells were stained with a solution of 4% aqueous Giemsa stain in phosphate buffer (pH 7.0). Foci of transformed cells were then visible by eye due to their high local density and verified by under light microscopy.

Subcellular Fractionation:

NIH 3T3 cells were cultured in DMEM containing 2% FBS with PMA and ibuprofen (10 μg/ml) in duplicate for 30 min, 4 hours, 18 hours, 48 hours and 2 weeks, respectively. The cells were washed twice with phosphate-buffered saline (PBS) at 37° C. and subsequently lysed and scraped in 1 ml ice-cold protein lysis buffer (20 mM Tris-HCl, pH7.4, 2 mM EGTA, 2 mM EDTA, 25 mg/ml leupeptin and 25 mg/ml aprotinin) at 4° C. After combining cells from duplicate dishes, cellular fractionation was performed according to the methods of Leach et al. (1989). Briefly, cells were homogenized 10× in 15 ml glass homogenizer with a tight-fitting pestle and centrifuged at 900×g for 10 min. The resulting supernatant was then centrifuged at 100,000×g for 60 min to produce a nucleus-free membrane fraction (pellet) and a cytosol fraction (supernatant) for Western blots. The 900×g nuclear pellet was suspended in the 2 ml lysis buffer containing 10% sucrose and 0.1% Triton X-100 and washed twice by centrifuging at 1000×g for 10 min, then resuspended in 1 ml of the same buffer without Triton X-100 for Western blots. The purity of the fractions was monitored by light microscopy. The hippocampus and neocortex of rat brain were similarly fractionated using the technique described by Leach et al., (1989). The protein concentrations were determined by the method of Lowry et al. (1951). The samples were stored at −70° C. until analysis.

Western Blot Analysis:

15 μl of human plasma, 15 μl of rat plasma, CSF or 50 μg of rat brain protein were denatured with 35 μl of sample buffer at 95° C. for 4 min. Denatured proteins were separated by 10% SDS-polyacrylamide gel electrophoresis with a 50 μg or 20 μg protein load for each sample for APPs or PKC, respectively, and electrophoretically transferred from gel to nitrocellulose membrane. Nonspecific binding of antibody to the membrane was blocked by 1 h incubation with 5% nonfat milk (Carnation, Nestle, Glendale, Calif.) and 0.1% Tween 20 in blocking buffer (20 mM Tris-HCl, pH 7.4 with 2.7% NaCl). Following 30 min washes (10×3), the blocked membranes were incubated with anti-APP (Clone 22C11, Boehringer Mannheim, Indianapolis, Ind.) or anti-PKC, α, βII, θ, ε, ξ, γ (Life Technologies, Gaithersburg, Md.) antibody for 12 h at 4° C. and subsequently exposed to second antibody coupled to horseradish peroxidase for 1 h after a 30 min washing. The immunoreactive bands were developed using enhanced chemilumenescence (ECL. Amersham Life Sci., Little Chalfont, UK), following extensive washing with the blocking buffer. The PKC bands were verified in each case by competitively blocking the signal with the peptide corresponding to each of PKCs. The bands were quantitated by scanning densitometry. Quantitative comparisons were made between samples processed simultaneously on one blot.

Protein Kinase C Activity Assay:

The assay for PKC activity was carried out essentially as described by Boyle et al.(1991) by quantifying the phosphorylation of histone in the presence of phoshatidylserine and PMA, with or without ibuprofen. Incubation mixtures contained 20 mM Hepes, pH 7.4, 0.34 mM EDTA, 0.34 mM EGTA, 1.67 mM CaCl2, 10 mM MgCl2, 0.15 mM 32P-γ-ATP (0.05 mCi/ ml; New England Nuclear, Boston, Mass.), 2 mg/ml histone, 60 μg/ml phosphatidylserine, 200 ng/ml PKC and R-, S-, or racemic ibuprofen (0.02 to 20 μM) in a final volume of 100 μl. Following 2 min initial incubation at 30° C., kinase reactions were initiated by the addition of $^{32}$P-γ-ATP and enzyme and continued at 30° C. for 2 min. Control incubations contained all assay components except enzyme and ibuprofen. The reactions were terminated with 2 ml ice cold 1.5% phosphoric acid. All samples were carried out in duplicate. The phosphorylated histone was transferred to the nitrocellulose membrane and washed 3 times with 2 ml 1.5% phosphoric acid and radioactivity counted (LS3801, Beckman).

HPLC Analysis:

The concentration of the enantiomers of ibuprofen in cell culture media was determined by an HPLC procedure previously described for the enantiomers of ketoprofen (Grubb et al., 1996). The HPLC column consisted of a 5 μm (S,S)-Whelk-O1 stationary phase (250 mm×4.6 mm; Regis Technologies, Morton Grove, Ill.) eluted with a mobile phase of hexane/isopropyl alcohol/acetic acid (98/2/0.05) flowing at 0.8 ml/ min. R- and S-ibuprofen were eluted at 13 and 16 min respectively. Quantitation was achieved using peak area ratios with R-flurbiprofen as internal standard and ultraviolet absorbance at 254 nm. The limit of quantitation was set at 100 ng/ml.

Rat Treatment with Ibuprofen.

Male Sprague-Dawley rats (12 month) were obtained from Harlan-Sprague-Dawley, Inc. (Indianapolis, Ind.) and housed under controlled conditions of temperature humidity and light/dark cycle. 16 rats were divided into four equal groups and given 0.9% NaCl (control), racemic, R- or S-ibuprofen at dose 10 mg/kg body weight bid for 7 days. Rat blood, brain and 50 µl of cerebrospinal fluid were collected and stored at −70° C. for APPs and PKC analysis by Western blotting. Rat stomach and duodenum were collected for the quantitation of gastroduodenal lesions.

Human Treatment with Ibuprofen.

Subsequent to approval of the study protocols by the Institutional Review Board of Indiana University, 4 healthy nonsmoking, medication-free subjects (ages of 19–40 years) were enrolled study to examine the pharmacokinetics and of ibuprofen effect on APPs secretion following the administration of racemic or S-ibuprofen.

After overnight fasting, a control blood sample was taken and 800 mg of racemic or S-ibuprofen was administered orally. Food intake was restricted until 4 h post dose. Blood samples (14 ml each) were obtained at 1, 3, 8, 12 and 24 h post dose. Over the next 6 days, ibuprofen was administered as 800 mg t.i.d. and subjects were instructed to return on day 3 and 5 for a single blood draw. On the morning of day 8 subjects after fasting overnight were given their final 800 mg dose of ibuprofen and blood samples were obtained 1 h, 1, 2, 3, 4, 7 and 14 days post final dose. Serum samples were stoiced −20° C. prior to analysis. The washout time was at least 2 months between racemic and S-ibuprofen dosing.

Tissue Preparation and Ouantitation of Gastroduodenal Lesions.

The rat stomach and first 12 cm of the duodenum were opened and carefully shed with saline to remove any residual debris and fixed in 10% buffered formaldehyde. Tissues were examined macroscopically (×10) for lesions and hemorrhages. The evaluation of lesions or hemorrhages was based on the ulcer index (UI) reported by Leyck et al. (1985) and expressed as the sum total of lesions per treatment. The scoring units used ranged from 0 to 5, where zero represents no macroscopically visible lesions; 1 represents one to three small ulcers less than 4 mm; 2 represents more than three small ulcers; 3 represents ulcer hemorrhages with several small ulcers; 4 represents large (>4 mm) ulcers; 5 indicates tissue perforation.

Example 2

Enantioselective Inhibition of Neoplastic Transformation by Ibuprofen

Figure 1A:
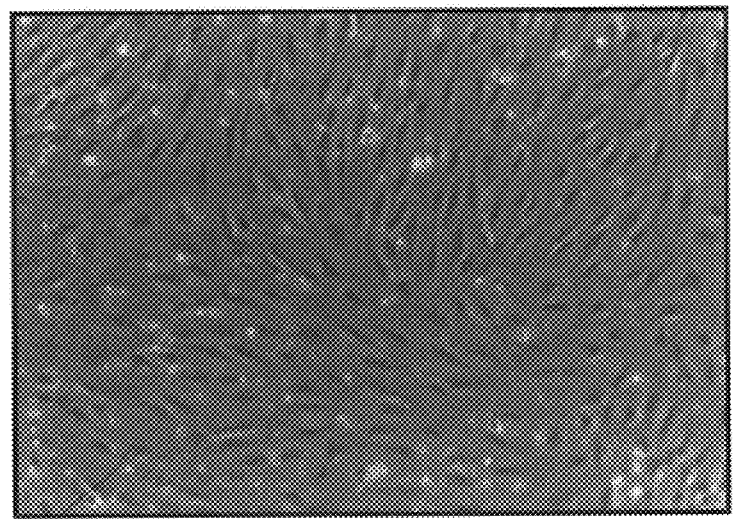
Figure 1B:
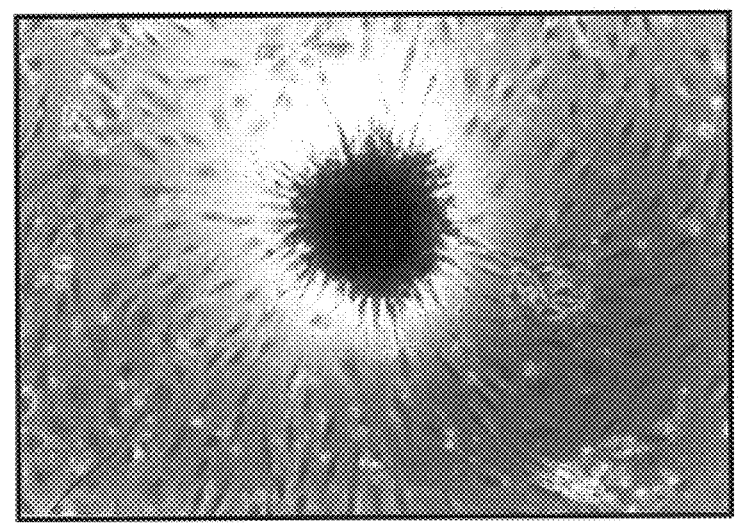
Figure 1C:
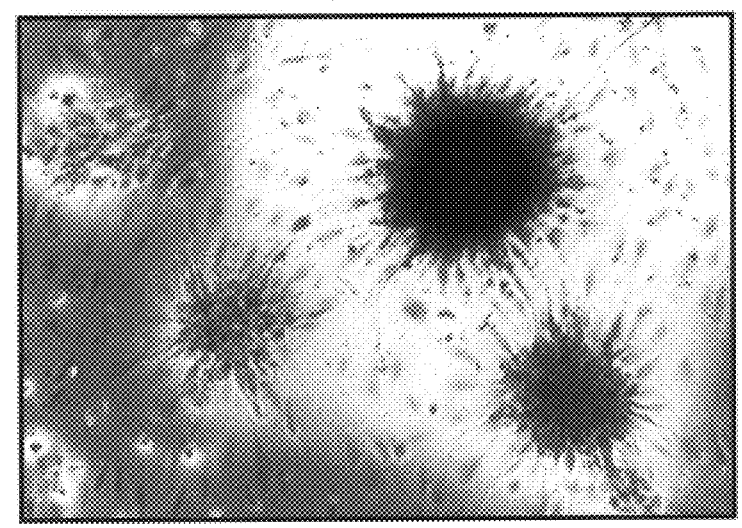
Figure 1D:
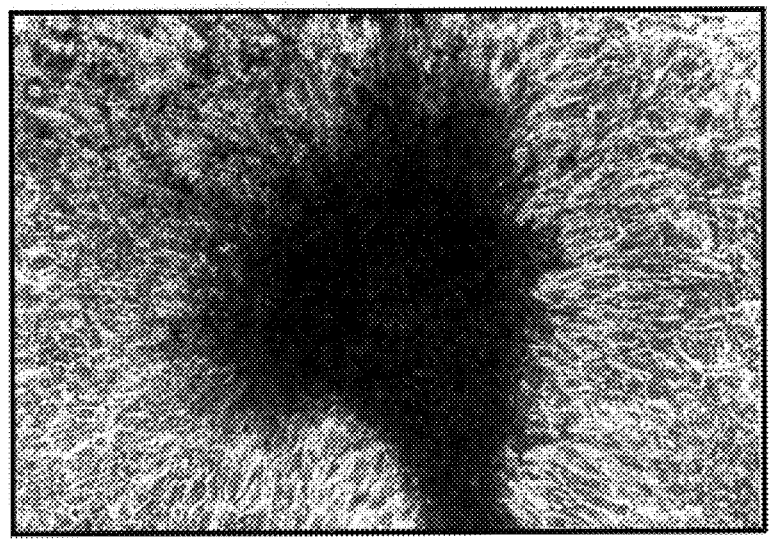
Figure 2:
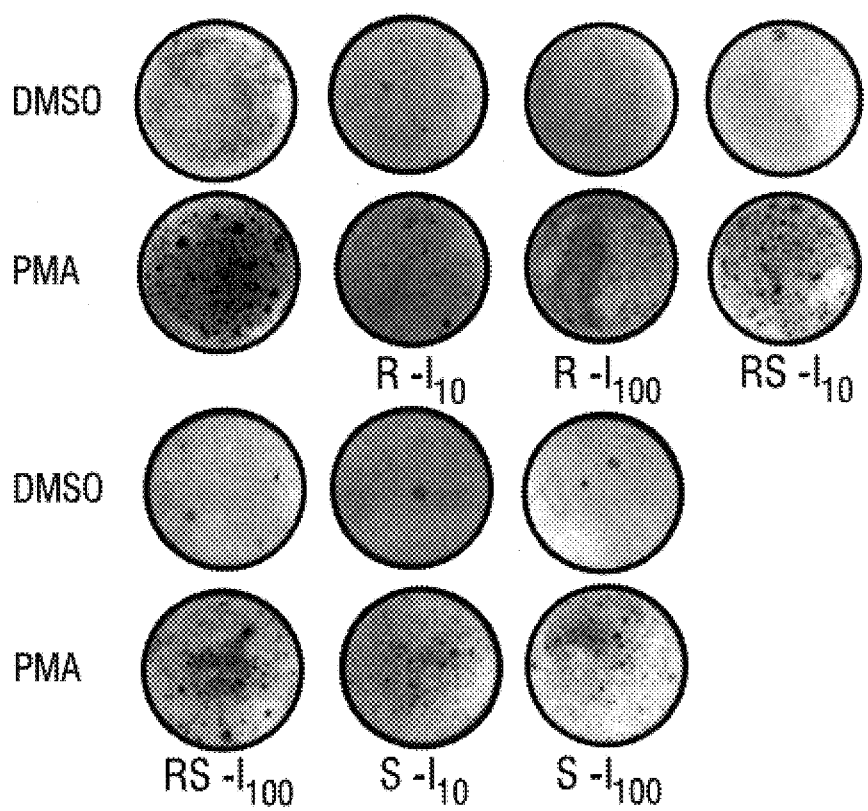
FIG. 2. Influence of R-ibuprofen (R-I), S-ibuprofen (S-I) and racemic ibuprofen (Rac-I) on PMA induced neoplastic transformation of NIH 3T3 cells as measured by foci formation. Cells in stationary culture with 2% FBS in DMEM and PMA (0.02 µg/ml) were treated with 10 or 100 µg/ml ibuprofen. DMSO controls were exposed to vehicle with and without ibuprofen but not PMA. Following 6 weeks culture cells in 35 mm culture dishes were fixed and stained with Giemsa reagent.

Wild NIH 3T3 cells cultured to stationary phase in DMEM with 10% FBS underwent morphological transformation when exposed to 2% FBS and PMA at 0.02 µg/ ml for prolonged periods. The cells treated with PMA for 6 days lost contact inhibition and grew in a multilayer pattern (FIG. 1A), which was in marked contrast to the confluent monolayer of untreated cells when viewed with phase contrast microscopy. Distinct foci formation of the cells was observed at 12 and 18 days culture with PMA. Foci consisted of heaped masses that grew in an irregular pattern that was readily distinguished with light microscopy (FIG. 1B and FIG. 1C). The foci of transformed cells grew slowly for the first 3 weeks and some of them were visible by eye after 21 days culture (FIG. 1D). Following 4 weeks of culture in the presence of PMA, the foci grew quickly and occupied over 50% of the dish area at 6 weeks (FIG. 2).

To examine the effect of R-, S- and racemic ibuprofen on the neoplastic transformation of NIH 3T3 cells, stationary culture cells were exposed to 2% FBS in DMEM and PMA (0.02 µg/ml) and two ibuprofen concentrations for 6 weeks. Racemic ibuprofen and both enantiomers dramatically decreased the PMA induced foci formation of NIH 3T3 cells in a concentration independent manner (FIG. 2). Interestingly, the capability of the enantiomers of ibuprofen to inhibit foci formation was more pronounced than that of the racemate (FIG. 2). Control incubations lacking PMA but containing DMSO vehicle with and without ibuprofen showed no effect on NIH 3T3 cell growth patterns (FIG. 2). No inversion of R- to S-ibuprofen was detectable under these experimental conditions.

Figure 3:
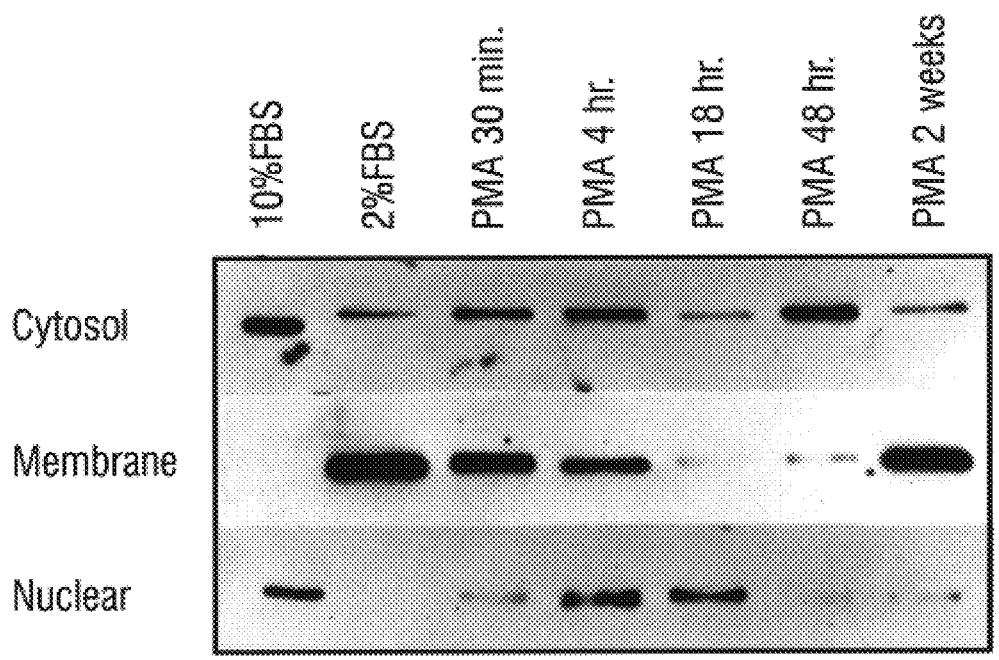
FIG. 3. Western blots of the time course of PKCα distribution in cytosol, membrane and nuclear fractions. Blots were obtained from control NIH 3T3 cells grown to confluence in 10% FBS (10% FBS) and cells exposed to: 2% FBS for 30 min (2% FBS); 2% FBS plus PMA (0.02 µg/ml) for 30 min (PMA 30 min.); 2% FBS plus PMA for 4 hr (PMA 4 hr.); 2% FBS plus PMA for 18 hr (PMA 18 hr.); 2%

The cytosolic, membrane and nuclear fractions were obtained by differential centrifugation from of NIH 3T3 cells grown to confluence in 10% FBS and from cells which were exposed to a 2% FBS media and PMA (0.02 µg/ml) for up to 14 days (FIG. 3). The latter subcellular fractions were subjected to denaturing SDS-polyacrylamide gel electrophoresis followed by blotting onto the nitrocellulose membranes. The membranes were probed for presence of PKCα by means of a anti-PKCα polyclonal antibody raised to the peptide sequence corresponding to amino acids 313–326 of PKCα. The immunoreactive band of PKCα was verified by using a PKCα specific peptide to block the binding of PKCα to the antibody. In cultures employing 10% FBS media, PKCα could be only detected in the cytosolic compartment of NIH 3T3 cell. The ability to detect PKCα in the membrane compartments under these conditions was established by spiking the protein into a nuclear membrane preparation (FIG. 3).

Compared to 10% FBS control the substitution by 2% FBS media for 30 min resulted in translocation of PKCα to the membrane fraction (FIG. 3). The latter intracellular translocation of PKCα from soluble cytoplasmic protein to membrane-associated form is thought to reflect physiological activation. Prolonged exposure to 2% FBS media alone resulted in a loss of PKCα from membrane and cytosolic compartments without a corresponding appearance in the nuclear membrane (FIG. 4). When cells were exposed to PMA (0.02 µg/ml) in addition to 2% FBS media for 30 min there was again a translocation of PKCα to the membrane fraction and some indication of PKCα appearing in the nuclear fraction (FIG. 3). Following 4 hours exposure to PMA there was a clear association of PKCα with the nuclear fraction that remained at 18 hours despite its disappearance from the membrane and cytosolic fractions (FIG. 3). At 48 hours exposure to PMA, cytosolic PKCα had been regenerated but membrane and nuclear sites were not. Finally, at 2 weeks of PMA exposure there was again translocation from cytosol to membrane fractions, but interestingly translocation to the nuclear compartment was absent (FIG. 3). The latter translocation of newly synthesized PKCα to the membrane but not nuclear sites corresponds to the appearance of the neoplastic foci noted above.

R-, S- and racemic ibuprofen clearly modulated the time dependent intracellular redistribution of PKCα following exposure of NIH 3T3 cells to 2% FBS and PMA (0.02 µg/ml). Both R- and S-ibuprofen (10 µg/ml) reduced the cytosol to membrane PKCα translocation induced by PMA after 30 min, 4 hours and 2 weeks of exposure (FIG. 4). At 4 hours of exposure to PMA, R-ibuprofen was more effective than its antipode in inhibiting PKCα translocation.

Racemic ibuprofen (10 μg/ml) was less potent than either of the enantiomers with respect to inhibiting PKCα translocation (FIG. 4). The latter was particularly evident following 2 weeks of PMA exposure when PKCα was detectable in the membrane fraction for the racemate but not the individual isomers. Racemic ibuprofen and the individual enantiomers completely blocked PKCα translocation from the cytosol to nuclear compartments induced by exposure to PMA for 4 hours.

The capability of ibuprofen to directly modulate PKC activity stimulated by PMA was studied by using a partially purified PKC preparation from rat brain that consisted predominantly of PKCα. Racemic ibuprofen inhibited PKC mediated histone phosphorylation at 2 μM, whereas the R- or S-enantiomers were effective at 1 μM (FIG. 5). Maximal inhibition of PKC activity was 59, 53 and 62% and occurred at 20 μM racemic, R- and S-ibuprofen respectively. This range of ibuprofen concentrations were chosen to reflect the estimated unbound concentration in culture media containing PBS (fraction unbound []0.05).

Example 3

R-Ibuprofen Prevents the Onset and Slows the Progression of Alzheimer's Disease

Both control and NSAID (50 μM) treated NIH 3T3 cell lines released APPs into the cell culture medium. The released APPs appeared as one major band on Western blots with an approximate molecular weight of 105 kDa. Only ibuprofen and fenoprofen showed an increased APPs secretion following a 20 h period of culture. A 1.5-, 2.1-, and 1.7-fold increase of APPs secretion was noted after 50 μM of racemic, R- and S-ibuprofen treatment for 20 h, respectively. A corresponding 1.6-, 1.3-, and 1.3-fold increase was noted for racemic, R- and S-fenoprofen treatment, respectively (Table 2). Aspirin failed to show an increased secretion of APPs in NIH 3T3 cell lines.

TABLE 2

Effect of NSAIDs (50 μM) on APPs secretion by
NIH 3T3 cell lines (n = 2) in 20 h culture (mean ± S.D)
Density of APPs band

| | |
|---|---|
| Control | 3.99 ± 0.86 |
| RS-Ibuprofen | 6.073 ± 0.55 |
| R-Ibuprofen | 8.34 ± 0.88 |
| S-Ibuprofen | 6.83 ± 0.31 |
| RS-Ketoprofen | 3.67 ± 0.27 |
| R-Ketoprofen | 3.41 ± 0.39 |
| S-Ketoprofen | 2.99 ± 0.57 |
| Aspirin | 2.92 ± 0.43 |
| RS-Ketoprofen | 2.94 ± 0.98 |
| R-Ketoprofen | 2.74 ± 0.34 |
| S-Ketoprofen | 3.76 ± 1.26 |
| RS-Fenoprofen | 6.36 ± 0.77 |
| R-Fenoprofen | 5.32 ± 1.29 |
| S-Fenoprofen | 5.32 ± 1.53 |
| RS-Flubiprofen | 3.07 ± 0.34 |
| R-Flubiprofen | 3.30 ± 0.81 |
| S-Flubiprofen | 2.37 ± 0.66 |
| R-Naproxen | 3.34 ± 0.41 |
| S-Naproxen | 2.78 ± 0.79 |
| Proxicam | 3.29 ± 0.77 |

To examine the effect of ibuprofen on brain APPs secretion, 12 month-old rats were given racemic, R- or S-ibuprofen (10 mg/kg, P.O. bid) for 7 days. The cytosolic and membrane fractions were obtained by differential centrifugation of rat brain tissue treated by ibuprofen. The latter subcellular fraction and CSF were subjected to denaturing SDS-polyacrylamide gel electrophoresis followed by blotting onto nitrocellulose membranes. The membranes were probed for presence of APPs by means of an anti-APP (clone 22C11) antibody to react with amino acids 60–100 of the APP terminus. There was a single immunoreactive band for APPs with an approximate molecular weight of 105 kDa. Racemic ibuprofen and both enantiomers dramatically increased APPs secretion in rat CSF (FIG. 6). Interestingly, the capability of the R-enantiomer of ibuprofen to increase APPs secretion was significantly greater than that of the racimate and S-enantiomer (Table 3). In the same fashion, ibuprofen increased the content of cytosolic APPs of rat brain and R-ibuprofen was more potent than racemic or S-ibuprofen (FIG. 7). Correspondingly, ibuprofen decreased content of membrane APP of rat brain, but not significantly (FIG. 8).

TABLE 3

Effect of racemic. R- or S-ibuprofen on APP content in CSF,
cytosol and membrane fractions of rat brain (n = 4 mean ± S.D.)
Density of APP Bands

| | CSF | Cytosol | Membrane |
|---|---|---|---|
| Control | 8.60 ± 3.87 | 8.2 ± 3.99 | 5.37 ± 1.96 |
| RS-Ibuprofen | 13.63 ± 6.56* | 9.32 ± 5.35 | 4.65 ± 1.17 |
| R-Ibuprofen | 19.48 ± 8.31*, # | 11.51 ± 5.89 | 4.85 ± 1.52 |
| S-Ibuprofen | 11.91 ± 6.42* | 10.29 ± 5.75 | 3.99 ± 1.39 |

*$p < 0.05$, compared
$p < 0.05$, compared to racemic or S-ibuprofen

Racemic, R- and S-ibuprofen clearly modulated the APPs secretion in rat brain. The capability of ibuprofen to increase APPs secretion from brain may reflect the activation of rat brain PKCs. Following separation of cytosolic or membrane proteins of rat brain protein by SDS-polyacrylamide gel electrophoresis, the proteins were transfer to nitrocellular membranes. The membranes were then probed for presence of PKCs using polyclonal antibodies against PKC α, βII, θ, ε, ξ, or γ. The immunoreactive band of each PKC was verified by using PKC specific peptides to block the binding of PKC to a given antibody.

In control rat brain, PKC α and βII were mainly located in the membrane compartment when 20 μg protein of cytosolic and membrane was applied to SDS-polyacrylamide gel, which is consistent with the localization of PKC α or βII in the membranous fraction of normal human brain (Shimohama and Matsushima, 1995). After 7 days of treatment, R-ibuprofen increased rat brain membranous fraction PKC α and βII dramatically; S- and racemic ibuprofen also increased PKCα and βII content in rat brain but not significantly (FIG. 9, FIG. 10 and Table 4). PKC α is believed to be the major isotype of PKC isozyme to regulate APPs secretion. When PKC α is overexpressed or activated, APPs secretion increased dramatically in fibroblasts cell lines (Slack et al., 1993; Cutting et al., 1991). Other PKC isozymes, such as PII, may also regulate APPs metabolism. In the brain of AD patients, PKC a and PII are significantly decreased. However, racemic, R- and S-ibuprofen did not show a dramatic effect on PKC θ, ε, γ, ξ, content of cytosolic or membranous fractions of rat brain.

TABLE 4

Effect of racemic, R- or S-ibuprofen on PKC α or βII
content in membrane fraction of rat brain (n = 4 mean ± S.D.)
Density of PKC α of βII Bands

|  | PKC βII | PKC α |
| --- | --- | --- |
| Control | 6.67 ± 1.79 | 11.56 ± 4.5 |
| RS-ibuprofen | 8.46 ± 3.68 | 13.61 ± 5.15 |
| R-ibuprofen | 9.69 ± 2.19* | 18.41 ± 3.46* |
| S-ibuprofen | 5.99 ± 3.96 | 16.58 ± 4.44 |

*$p < 0.05$, compared to control

Denatured human serum from racemic or S-ibuprofen treated subjects was subjected to SDS-polyacrylamide gel electrophoresis followed by transfer onto nitrocellulose membranes. The membranes were subsequently probed for presence of APPs by a anti-APP (clone 22C11) antibody. One of immunoreactive bands of APPs was identical to that in rat brain and CFS with an approximate molecular weight of 105 kDa as previously reported (Bush et al., 1993). In humans treated with racemic ibuprofen there was an increase in APPs (105 kDa band) secretion into plasma for 24 h after a single oral 800 mg dose and an increased secretion for 14 days after dosing for 7 days (800 mg, three times daily, orally; FIG. 11 and FIG. 12). However, in the same dosing range of S-ibuprofen, APPs (105 kDa band) secretion was only increased for 3 h and 1 day following single 800 mg or 7 days (800 mg t.i.d.) oral treatment respectively (FIG. 13 and FIG. 14, Table 6).

TABLE 5

Gastric Ulcer Index of
Racemic R- or S-ibuprofen treated rat (n = 4)
Ulcer Index

|  | 1 | 2 | 3 | 4 | Total |
| --- | --- | --- | --- | --- | --- |
| Control | 0 | 0 | 0 | 0 | 0 |
| RS-ibuprofen | 3(B1)* | 6 | 7 | 11 | 27(B1)** |
| R-ibuprofen | 1 | 1 | 0 | 0 | 2 |
| S-ibuprofen | 11(B4) | 9(B2) | 4 | 4 | 28(B6)** |

*Bleeding site
**$p < 0.001$, compared with control and R-ibuprofen

TABLE 6

Effect of ibuprofen on human blood
APPs (105 kDa) (n = 4, mean ± S.D.)

| | Post 1st dose (800 mg) | | Post 7 days dose (800 mg, tid) | |
| --- | --- | --- | --- | --- |
| | RS-Ib | S-Ib | RS-Ib | S-Ib |
| 0 (hour) | 1.95 ± 1.29 | 1.76 ± 0.74 | 0 (hour) | 2.46 ± 0.87 | 0.96 ± 0.64 |
| 1 | 3.64 ± 0.62 | 2.53 ± 0.78 | 1 (hour) | 4.57 ± 2.93 | 2.61 ± 1.84 |
| 3 | 3.22 ± 0.45 | 2.29 ± 1.38 | 1 day | 6.15 ± 2.77 | 2.98 ± 2.06 |
| 8 | 2.47 ± 1.45 | ND# | 2 days | 4.77 ± 2.95 | ND |
| 12 | 2.125 ± 1.31 | ND | 3 days | 4.33 ± 2.61 | ND |
| 24 | 2.25 ± 1.10 | ND | 4 days | 3.37 ± 2.22 | ND |
|  |  |  | 7 days | 3.21 ± 1.88 | ND |
|  |  |  | 14 days | 3.77 ± 0.95 | ND |

Not detectable

Human blood contains forms of APP of similar size to those released by platelet. The platelet is a major source of circulating APPs and A((Bush et al., 1993; Chen et al., 1995). The different effects of racemic or S-ibuprofen on APPs (105 kDa) secretion in human into blood may reflect the activation of platelet PKC α. In the inventors' previous study, R-ibuprofen caused complete translocation of PKC a from human platelet cytosol to membrane fractions, but the S-enantiomer did not. The stronger increase of APPs (105 kDa) secretion by racemic ibuprofen most likely results from the stronger activation of PKC α by R-ibuprofen.

Although the use of NSAIDs prophylactically actually offers promise as a strategy for the prevention or delay in onset of AD (Breitner et al., 1994; Breitner et al., 1995; Rich et al., 1995; Rogers et al., 1993; Stewart et al., 1997), the potentially serious adverse events, such as gastropathy, during chronic use is a major concern. NSAID induced gastropathy is characterized by subepithelial hemorrhage, erosions, and ulcers. Approximately 50% of patients taking NSAIDs regularly have gastric erosions and 10% to 30% have gastric ulcers (Laine, 1996). Most studies showed that NSAID use causes more gastric than duodenal ulcers. In the inventors' study, racemic and S-ibuprofen induced serious gastric ulcers and hemorrhage in rats following 7 days of treatment. In contrast, R-ibuprofen only caused one small gastric ulcer in 2 out of 4 rats. There was no ulcer larger than 4 mm. Overall R-ibuprofen caused significantly less serious gastropathy (ulcer plus hemorrhage) than both racemic and S-ibuprofen.

The inventors' data demonstrate, the R-enantiomer of ibuprofen is significantly more active than the currently employed racemic ibuprofen and S-ibuprofen in the secretion of APPs and therefore more effective in preventing the onset and slowing the progression of AD.

Furthermore, R-ibuprofen is safer than racemic or S-ibuprofen because it causes significantly less gastropathy.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions, and in the steps or in the sequence of steps of the methods described herein, without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abramson, et al., "Non-steroidal anti-inflammatory drugs: effects on a GTP binding protein within the neutrophil plasma membrane," *Biochem. Pharmacol.*, 41:1567–1573, 1991.

Anderson, et al., "Exact cleavage site of Alzheimer amyloid neurosci," *Lett.*, 128:126–128, 1991.

Angel and Karin, "The role of jun, fos and the AP-1 complex in cell proliferation and transformation," *Biochim. Biophys. Acta*, 1072:129–157, 1991.

Bautista, et al., "In vivo latex phagocytosis primes the Kupffer cells and hepatic neutrophils to generate superoxide anion. J. Leukocyte," *Biol.*, 51:39–45, 1992.

Bishop, et. al., "The molecular genetics of cancer," *Science*, 235:305–311, 1987.

Bomalaski, et al., "Aspirin inhibits phospholipase C," *Biochem. Bioph., Res. Co.*, 139:115–121, 1986.

Boneberg, et al., "Inhibition of cyclooxygenase-1 and -2 by R(-)- and S(+)-ibuprofen," *J Clin. Pharmacol.*, 36:16S-19S, 1996.

Boyle, et al., "Activation of protein kinase C decreases phosphorylation of c-jun at sites that negatively regulate its DNA-binding activity," *Cell*, 64:573–584, 1991.

Breitner, et al., "Anthony. Inverse association of antiinflammatory treatments and Alzheimer's disease," *Neurology*, 44:227–232, 1994.

Breitner, et al., "Delayed onset of Alzheimer's Disease with nonsteroidal Anti-inflammatory and histermine Hs Blocking Drugs," *Neurobiology of Aging*, 16:523–530, 1995.

Broda et al., "NSAIDs: A profile of Adverse Effects" Hanely and Belfus, Inc. Philadelphia, Pa., 1992.

Buckley et al., *Drugs*, 39(1): 86–109, 1990.

Bush, et al., "The, A4 amyloid protein precursor in human circulation," *Annals New York Academy of Sciences*, 695:175–82, 1993.

Caldwell et al., *Biochem. Pharmacol.*, 37: 105–114, 1988.

Caporaso, et al., "Protein phosphorylation regulates secretion," *Proc. Nation. Acad Sci. USA*, 89:3055–3059, 1990.

Castagna et al., 1982, Takai, Kaibuchi, Sano, Kikkawa, Nishizuka, "Direct activation of calcium-activated, phospholipid-dependent protein kinase by tumor promoting phorbol-esters," *J. Biol. Chem.*, 257:7847–7851, 1982.

Chen, et al., "Platelets are the primary source of Amyloid, -peptide in human blood," *Biochem. Biophy. Res. Commu.*, 213:96–103, 1995.

Cole, et al., "Decreased level of protein kinase C in Alzheimer Brain," *Brain Res.*, 452:165–174, 1988.

Craven, et al., "Role of local prostaglandin synthesis in the modulation of proliferative activity of rat colonic epithelium," *J. Clin. Invest.*, 72:1365–1375, 1983.

Dotto, et al., "Specific growth response of ras-transformed embryo fibroblasts to tumor promoters," *Nature*, 318:472–475, 1985.

Driedger and Blumberg, "The effect of phorbol diesters on chicken embryo fibroblasts," *Cancer Res.*, 37:3257–3265, 1977.

Esch, et al., "Cleavage of amyloid, peptide during constitutive processing of its precursor," *Science*, 248:1122–1224, 1990.

Everett et al., "Aryl-2-halogenoalkyamine. Pt. XII. Some carboxylic derivatives of NN-di-2-chloroethylaniline" *J. Chem. Soc.* 3: 2386–2392, 1953.

Flier and Underhill, "Amyloid and the pathogenesis of Alzheimer's disease," *New Engl. J. Med.*, 325:1849–1857, 1991.

Giovannucci, et al., "Aspirin and the risk of colorectal cancer in women," *N. Engl. J. Med.*, 333:609–614, 1995.

Glassman et al., "Spatial working memory score of humans in a large radial maze, similar to published score of rats, implies capacity close to the magical number 7 +/−22." *Brain Res. Bull.*, 34 (2) p151–9, 1994.

Goldegraber, et al., "Characterization and chromosomal localization of a cDNA on cooling brain amyloid of Alzheimer's Disease," *Science*, 235:877–880, 1987.

Grubb, et al., "Enantioselective analysis of ketoprofen and ketoprofen glucuronide in hemodialysis patients," *J. Chromatogr. B*, 678:237–244, 1996.

Hall and Xiaotao, "The role of coenzyme A in the metabolic fate of 2-arylpropionic acid NSAIDs," *Chem-Biol. Interact.*, 90:235–251, 1994.

Heath et al., "Non-steroidal antiinflammatory drugs and human cancer" *Cancer* 74 (10) 2885–2888, 1994.

Heath, et al., "Nonsteroidal antiinflammatory drugs and human cancer," *Cancer* 74:2885–2888, 1994.

Hixson, et al., "Antiproliferative effect of nonsteroidal anti-inflammatory drugs against human colon cancer cells," *Cancer Epidem. Biomar.*, 3:433–438, 1994.

Hunter and Karin, "The regulation of transcription by phosphorylation," *Cell*, 70:357–387, 1992.

Jabert and Castonguay, "Effects of NSAIDs on NNK-induced pulmonary and gastric tumorigenesis in A/J mice," *Cancer Lett.*, 66:21–28, 1992.

Kaiser et al., *J. Pharm. Sci.* 65(2), 269–273, 1976.

Kinouchi, et al., "Conventional protein kinase C—(and novel PKC (, but—(, increase the secretion of an N-terminal fragment of Alzheimer's Disease amyloid precursor protein from PKC cDNA transfected 3Y1 fibroblasts", *FEBS Lett (Netherlands)* 364:(2)203–206, 1995.

Kopp and Ghosh, "Inhibition of NF-κB by sodium salicylate and aspirin," *Science* 265:956–959, 1994.

Laine, "Nonsteroidal anti-inflammatory drug gastropathy," *Gastrointestinal Endoscopy Clinics of North America*, 6:489–504, 1996.

Lamph, et al., "Induction of proto-oncogene JUN/AP-1 by serum and TPA," *Nature*, 334:629–631, 1988.

Langman, et. al., "Risks of bleeding peptic ulcer associated with individual non-steroidal anti-inflammatory drugs," *Lancet*, 343:1075–1078, 1994.

Leach, et al., "Type 3 protein kinase C localization to the nuclear envelope of phorbol ester-treated NIH 3T3 cells," *J. Cell Biol.*, 109:685–695, 1989.

Leyck, et al., "Improvement of gastric tolerance of nonsteroidal anti-inflammatory drugs by polyene phosphatidylcholine," *Eur. J Pharm.*, 117:35–42, 1985.

Love, et al., "Levels of ornithine decarboxylase activity in patients with colon cancer, a family history of nonpolyposis hereditary colorectal cancer, and adenomas," *Cancer Epidem. Biomar.*, 1:195–198, 1992.

Lowry, et al., "Protein determination with the Folin phenol reagent," *J. Biol. Chem.*, 193:265–275, 1951.

Marnett, "Aspirin and the potential role of prostaglandins in colon cancer," *Cancer Res.*, 52:5575–5589, 1992

Mashiah, et al., "Protein kinase C alteration is an early biochemical marker in Alzheimer's Disease," *J. of Neurosci.*, 11:2759–2767, 1991.

Masters, et al., "Amyloid plague care protein in Alzheimer's disease and Downs Syndrome," *Proc. Natl. Acad Sci. USA*, 82:4245–4249, 1985.

Matsushima, et al., "Ca+-Dependent and Ca+-independent protein kinase C changes in the brains of patients with Alzheimer's Disease," *J. of Neurochem.*, 67:317–323, 1996.

Metha, et al., "Influence of thiols and inhibitors of prostaglandin biosynthesis on the carcinogen-induced development of mammary lesions in vitro," *Anticancer Res.,* 11:587–591, 1991.

Metha, et al., "Influence of thiols and inhibitors of prostaglandin biosynthesis on the carcinogen-induced development of mammary lesions in vitro," *Anticancer Res.,* 11:587–591, 1991.

Mischak, et al., "Overexpression of protein kinase C-δ and -ε in NIH 3T3 cells induces opposite effects on growth, morphology, anchorage dependence, and tumorigenicity," *J. Biol. Chem.,* 268:6090–6096, 1993.

Murray, et al., "Effects of nonsteroidal anti-inflammatory drugs on glomerular filtration in elderly patients without and with renal insufficiency," *Am. J Med. Sci.,* 310:188–197, 1995.

Neidel, et al., "Phorbol ester receptor copurifies with protein kinase C," *Proc. Natl. Acad. Sci.,* 80:36–40, 1983.

Patterson, et al., "Activated neutrophils alter contractile properties of the pulmonary artery," *Am. J. Resp. Cell Mol.,* 6:260–269, 1992.

Price, et al., "Amyloidosis in aging and Alzheimer's disease," *Am. J. Pathol.,* 141:767–772, 1992.

Reddy, et al., "Inhibition of colon carcinogenisis by prostaglandin synthesis inhibitors and related compounds," *Carcinogenesis,* 13:1019–1023, 1992.

Rich, et al., "Nonsteroidal anti-inflammatory drugs in Alzheimer's Disease," *Neurology,* 45:51–54, 1995.

Robakis, et al., "Molecular cloning and characterization of a cDNA encoding the cerebrovascular and the neuritic plaque amyloid peptides," *Proc. Natl. Acad Sci. USA,* 84:4190–4194, 1987.

Rogers, et al., "Clinical trial of indomethacin in Alzheimer's Disease," *Neurology,* 43:1609–1611, 1993.

Rosser, M., "Molecular pathology of Alzheimer's disease" *J. Neurol. Neurosurg. Psych.* 56, 583–586, 1993.

Rubin and Rubin, "Selective nature of 12-myristate 13-acetate-induced neoplastic transformation in NIH 3T3 cells," *Proc. Natl. Acad. Sci.,* 91:2320–2323, 1994.

Rubin and Xu, "Evidence for the progressive and adaptive nature of spontaneous transformation in the NIH 3T3 cell line," *Proc. Natl. Acad. Sci.,* 86:1860–1864, 1989.

Rubin, et al., "Physiological induction and reversal of focus formation and tumorigenicity in NIH 3T3 cells," *Proc. Natl. Acad. Sci.,* 87:10005–10009, 1990.

Santoro, et al., "Inhibition of tumor growth in vivo and in vitro by prostaglandin E," *Nature,* 263:777–779, 1976.

Schoen and Vender, "Mechanisms of nonsteroidal anti-inflammatory drug induced gastric damage," *Am. J. Med.,* 86:449–458, 1989.

Shimohama and Matsushima, "Signal translocation mechanisms in Alzheimer Disease," *Alzheimer and Associated Disorders,* 9(S2):15–22, 1995.

Shimohama, et al., "Assessment of protein kinase C isozymes by two-site enzyme immunoassay in human brains and changes in Alzheimer's Disease," *Neurology,* 43:1407–1413., Sisodia, et al., "Evidence that, -amyloid protein in Alzheimer's Disease not derived by normal processing," *Science,* 248:492–495, 1990.

Slack, et al., "Regulation of Amyloid precursor protein release by protein kinase C in Swiss 3T3 fibroblasts," *Annals New York Academy of Sci.,* 695:128–131, 1993.

Smith and Rutledge "Chemotherapy in advanced ovarian cancer" *Nat'l Cancer Inst. Monogr.* 42:141–143, 1975.

Socci et al., "Nicotine enhances Morris water maze performance of young and aged rats." *Neurobiol. Aging,* 16 (5) p857–60, 1995.

Stewart, et al., "Risk of Alzheimer's disease and duration of NSAID use," *Neurology,* 48:626–632, 1997.

Szallasi, et al., "Differential regulation of protein kinase C isozymes by bryostatin I and phorbol 12-myristate 13-acetate in NIH 3T3 fibroblasts," *J. Biol. Chem.,* 269:2118–2124, 1994.

Tangi, et al., "Protease inhibitor domain encoded by an amyloid protein precursor mRNA associated with Alzheimer's Disease," *Nature,* 331:528–30, 1988.

Turner and Berkel, "Nonsteroidal anti-inflammaory drugs for the prevention of colon cancer," *Can. Med. Assoc. J.,* 149:595–602, 1993.

Vesela, et al., "Lack of inhibition of omithine decarboxylase activity by ibuprofen," *Pharmacol. Res.,* 25:347–352, 1992.

Villanueva, et al., "Equipotent inhibition by R(–)-, S(+)- and racemic ibuprofen of human polymorphonuclear cell function in vitro," *Br. J Clin. Pharmacol.,* 35:235–242, 1993.

Xiaotao, et al., "Incorporation of R- and S-ibuprofen in to hybrid diacylglycerols and stimulation of protein kinase C in vivo," Abstract, ISSX: 1996.

Yamaguchi et al., *Nippo. Yakurigaku Zasshi,* 90:295–302, 1987

Young et al., "advanced ovarian adenocarcinoma: a prospective clinical trial of melphalan (L-PAM) versus combination chemotherapy". *N. Engl. J Med* 299:1261–1266, 1978.

What is claimed is:

1. A method of preventing or slowing the onset of Alzheimer's disease, comprising administering to an animal in need thereof an amount of an R-ibuprofen pharmaceutical composition effective to inhibit onset of Alzheimer's disease in said animal, wherein said R-ibuprofen is substantially free from S-ibuprofen.

2. The method of claim 1, wherein said animal is a human subject.

3. The method of claim 1, wherein said R-ibuprofen pharmaceutical composition is administered orally.

4. The method of claim 1, wherein said R-ibuprofen pharmaceutical composition is administered at a dose of between 50 and 4000 mg per day.

5. A method of treating Alzheimer's disease, comprising administering to an animal with Alzheimer's disease a therapeutically effective amount of an R-ibuprofen pharmaceutical composition, wherein said R-ibuprofen is substantially free from S-ibuprofen.

6. The method of claim 5, wherein said animal is a human subject.

7. The method of claim 5, wherein said R-ibuprofen pharmaceutical composition is administered orally.

8. The method of claim 5, wherein said R-ibuprofen pharmaceutical composition is administered at a dose of between 50 and 4000 mg per day.

* * * * *